US009713687B2

(12) United States Patent
Leamon et al.

(10) Patent No.: US 9,713,687 B2
(45) Date of Patent: Jul. 25, 2017

(54) VENTILATOR AEROSOL DELIVERY SYSTEM WITH TRANSITION ADAPTER FOR INTRODUCING CARRIER GAS

(71) Applicant: Philip Morris USA Inc., Richmond, VA (US)

(72) Inventors: James Leamon, Warminster, PA (US); Timothy J. Gregory, Jamison, PA (US); Jan Mazela, Poznan (PL); Christopher Henderson, Solana Beach, CA (US)

(73) Assignee: Philip Morris USA Inc., Richmond, VA (US)

( * ) Notice: Subject to any disclaimer, the term of this patent is extended or adjusted under 35 U.S.C. 154(b) by 697 days.

(21) Appl. No.: 13/843,172

(22) Filed: Mar. 15, 2013

(65) Prior Publication Data

US 2014/0053831 A1 Feb. 27, 2014

Related U.S. Application Data

(60) Provisional application No. 61/732,082, filed on Nov. 30, 2012, provisional application No. 61/691,678, filed on Aug. 21, 2012.

(51) Int. Cl.
*A61M 11/00* (2006.01)
*A61M 15/00* (2006.01)
(Continued)

(52) U.S. Cl.
CPC .......... *A61M 15/009* (2013.01); *A61M 11/02* (2013.01); *A61M 11/041* (2013.01);
(Continued)

(58) Field of Classification Search
CPC ...... A61M 11/00; A61M 11/02; A61M 11/06; A61M 11/08; A61M 15/00; A61M 15/009;
(Continued)

(56) References Cited

U.S. PATENT DOCUMENTS 2,984,420 A * 5/1961 Hession, Jr. .......... B05B 7/0475 239/399
3,761,065 A * 9/1973 Rich .................... B01F 3/0473 261/116
(Continued)

FOREIGN PATENT DOCUMENTS

DE 1077828 B 3/1960
DE 92 04 938 8/1993
(Continued)

OTHER PUBLICATIONS

Nov. 19, 2013 Partial International Search Report issued in International Application No. PCT/EP2013/067421.

*Primary Examiner* — Kathryn E Ditmer
(74) *Attorney, Agent, or Firm* — Buchanan Ingersoll & Rooney PC

(57) ABSTRACT

A transition adapter component of a ventilator aerosol delivery system for delivering an aerosol to a patient, includes a housing having a proximal end and a distal end, the proximal end having an aerosol passage for receiving an aerosol produced by a heated capillary and a gas connection port for receiving carrier gas from a ventilator, which is in communication with a plurality of gas entry ports within the transition adapter. An inner cavity of the transition adapter receives the aerosol from the heated capillary and the streams of carrier gas from the plurality of gas exit ports within the transition adapter and directs the streams of carrier gas at least partially encircling and in parallel with the aerosol. An exit port on the distal end of the transition adapter housing delivers an entrained aerosol to an aerosol delivery connector.

38 Claims, 15 Drawing Sheets

(51) Int. Cl.

| | |
|---|---|
| ***A61M 16/10*** | (2006.01) |
| ***A61M 16/14*** | (2006.01) |
| ***B05B 7/00*** | (2006.01) |
| ***A61M 11/02*** | (2006.01) |
| ***A61M 16/00*** | (2006.01) |
| ***A61M 11/04*** | (2006.01) |
| ***A61M 11/06*** | (2006.01) |
| ***A61M 16/08*** | (2006.01) |
| ***B05B 7/04*** | (2006.01) |
| ***A61M 15/02*** | (2006.01) |

(52) U.S. Cl.
CPC ........... *A61M 11/042* (2014.02); *A61M 11/06* (2013.01); *A61M 15/0065* (2013.01); *A61M 15/025* (2014.02); *A61M 16/0057* (2013.01); *A61M 16/0833* (2014.02); *A61M 16/1045* (2013.01); *A61M 16/14* (2013.01); *B05B 7/045* (2013.01); *A61M 11/005* (2013.01); *A61M 2206/18* (2013.01)

(58) Field of Classification Search
CPC ...... A61M 16/08; A61M 16/10; A61M 16/12; A61M 16/14; A61M 16/16; B05B 1/34; B05B 1/3405; B05B 1/341; B05B 1/3415; B05B 1/3431; B05B 7/0075; B05B 7/04
See application file for complete search history.

(56) References Cited

U.S. PATENT DOCUMENTS 4,048,993 A 9/1977 Dobritz
4,121,583 A 10/1978 Chen
4,172,105 A 10/1979 Miller et al.
4,475,885 A * 10/1984 Finke ...................... F23C 7/002 239/424
4,532,088 A 7/1985 Miller
4,575,609 A 3/1986 Fassel et al.
4,960,992 A 10/1990 Vestal et al.
5,407,604 A 4/1995 Luffman
5,435,297 A * 7/1995 Klein .................. A61M 15/009 128/200.23
5,452,856 A 9/1995 Pritchard
5,713,971 A 2/1998 Rohrbach et al.
5,743,251 A 4/1998 Howell et al.
5,829,428 A 11/1998 Walters et al.
5,954,047 A * 9/1999 Armer ............... A61M 15/0086 128/200.14
6,003,512 A 12/1999 Gerde
6,014,890 A 1/2000 Breen
6,014,972 A * 1/2000 Sladek .............. A61M 15/0065 128/203.12
6,062,214 A * 5/2000 Howlett .............. A61M 15/009 128/200.14
6,095,505 A 8/2000 Miller
6,102,037 A 8/2000 Koch
6,234,459 B1 * 5/2001 Rock ...................... A61M 11/06 128/203.12
6,273,087 B1 * 8/2001 Boussignac ........... A61M 16/12 128/200.12
6,347,629 B1 * 2/2002 Braithwaite ...... A61M 15/0086 128/200.18
6,349,722 B1 2/2002 Gradon et al.
6,367,471 B1 * 4/2002 Genosar ............ A61M 15/0086 128/200.14
6,491,233 B2 12/2002 Nichols
6,501,052 B2 12/2002 Cox et al.
6,516,796 B1 2/2003 Cox et al.
6,526,976 B1 3/2003 Baran
6,557,551 B2 5/2003 Nitta
6,568,390 B2 5/2003 Nichols et al.
6,601,776 B1 8/2003 Oljaca et al.
6,615,826 B1 * 9/2003 Gabrio .............. A61M 15/0086 128/200.14
6,622,938 B2 9/2003 Fischer et al.
6,640,050 B2 10/2003 Nichols et al.
6,701,921 B2 3/2004 Sprinkel, Jr. et al.
6,701,922 B2 3/2004 Hindle et al.
6,715,487 B2 4/2004 Nichols et al.
6,772,757 B2 8/2004 Sprinkel, Jr.
6,779,521 B1 8/2004 Schmehl et al.
6,799,572 B2 10/2004 Nichols et al.
6,804,458 B2 10/2004 Sherwood et al.
6,923,179 B2 8/2005 Gupta et al.
7,066,452 B2 6/2006 Rotering et al.
7,077,130 B2 7/2006 Nichols et al.
7,107,987 B2 * 9/2006 Sundaram ......... A61M 15/0016 128/200.22
7,159,507 B2 1/2007 Grollimund et al.
7,167,776 B2 1/2007 Maharajh et al.
7,225,998 B2 6/2007 Pellizzari
7,428,902 B2 9/2008 Du et al.
7,500,479 B2 3/2009 Nichols et al.
7,518,123 B2 4/2009 Howell et al.
7,525,663 B2 4/2009 Kwok et al.
7,712,729 B2 5/2010 Kabasawa et al.
7,730,568 B2 6/2010 Wong et al.
7,802,569 B2 9/2010 Yeates et al.
7,905,229 B2 * 3/2011 Giroux .................. B05B 7/0869 128/200.18
7,938,113 B2 5/2011 Weinstein et al.
7,975,687 B2 7/2011 Grundler et al.
8,052,127 B2 11/2011 Nichols et al.
8,282,084 B2 10/2012 Nichols et al.
2003/0108342 A1 6/2003 Cox
2004/0124269 A1 * 7/2004 Dushkin ................... B05B 1/34 239/399
2004/0223918 A1 11/2004 Pham et al.
2005/0205084 A1 9/2005 Gupta et al.
2005/0235991 A1 10/2005 Cox
2006/0012057 A1 1/2006 Anthony
2006/0120968 A1 * 6/2006 Niven ............... A61M 15/0086 424/45
2006/0163570 A1 7/2006 Renn et al.
2008/0110458 A1 5/2008 Srinivasan et al.
2008/0299049 A1 * 12/2008 Stangl ............... A61M 15/0085 424/45
2009/0310950 A1 12/2009 Maharajh et al.
2010/0275909 A1 * 11/2010 Anderson ........... A61M 15/009 128/200.23
2011/0011395 A1 * 1/2011 Mazela ............. A61M 16/0816 128/202.13
2011/0011899 A1 * 1/2011 Yeates ............... A61M 15/0086 222/566
2011/0088696 A1 * 4/2011 Ratner .............. A61M 16/0816 128/205.24
2011/0259323 A1 * 10/2011 Crosby ............... A61M 15/009 128/200.14
2012/0138049 A1 * 6/2012 Wachtel ................. A61M 11/06 128/200.14

FOREIGN PATENT DOCUMENTS

| | | | |
|---|---|---|---|
| EP | 0624379 | A1 | 11/1994 |
| FR | 2543442 | A1 | 10/1984 |
| GB | 2 412 326 | A | 9/2005 |
| WO | 9742993 | A2 | 11/1997 |
| WO | 0138514 | A1 | 5/2001 |
| WO | 01/81182 | A2 | 11/2001 |
| WO | 03053502 | A1 | 7/2003 |
| WO | 03/099367 | A2 | 12/2003 |
| WO | 2005003547 | A1 | 1/2005 |
| WO | 2007076064 | A2 | 7/2007 |
| WO | WO 2009/117422 | A2 | 9/2009 |

* cited by examiner

Section B-B

Section A-A

Section C-C

Bubble CPAP Ventilator Aerosol Delivery System

Section B-B

Section C-C

Section A-A

SECTION A-A

SECTION B-B

VENTILATOR AEROSOL DELIVERY SYSTEM WITH TRANSITION ADAPTER FOR INTRODUCING CARRIER GAS

CROSS REFERENCE TO RELATED APPLICATIONS

This application claims priority under 35 U.S.C. §119(e) to U.S. Provisional Application No. 61/691,678, filed on Aug. 21, 2012, and U.S. Provisional Application No. 61/732,082, filed on Nov. 30, 2012, the entire contents of which are incorporated herein by reference thereto.

WORKING ENVIRONMENT

This disclosure relates to a transition adapter for delivery of aerosol from an aerosol generator, and a ventilator aerosol delivery system, which uses a portion of a ventilator's pressurized inspiratory gas flow to carry aerosol from the aerosol generator to a patient.

Patients, both adult and infants, in respiratory failure or those with respiratory dysfunction are often mechanically ventilated in order to provide suitable rescue and prophylactic therapy. A ventilatory circuit for administering positive pressure ventilation includes a positive pressure generator connected by tubing to a patient interface, such as a mask, nasal prongs, or an endotracheal tube, and an exhalation path, such as tubing that allows discharge of the expired gases, for example, to the ventilator.

The ventilation gas tube, expiratory flow tube and entrained aerosol tube can be connected to the patient interface via an aerosol delivery connector, for example, as disclosed in WO 2009/117422A2.

SUMMARY

In accordance with an exemplary embodiment, an aerosol transition adapter for delivering an aerosolized active agent to a patient comprises: a housing having a proximal end and a distal end, the proximal end having an aerosol passage for receiving an aerosol produced by a source of aerosol comprising an aerosolized active agent and the distal end having an exit port, the housing having a length between the distal end and the proximal end; a carrier gas connection port for receiving a carrier gas from a gas source, which is in communication with a plurality of carrier gas exit ports, the carrier gas exit ports are arranged adjacent to the aerosol passage in a pattern that partially encircles the flow of aerosol; an inner cavity, which is adapted to receive the aerosol from the aerosol passage and the carrier gas from the plurality of carrier gas exit ports and to direct the streams of carrier gas to at least partially encircle and flow in parallel with a main direction of a flow of the aerosol along the length of the housing toward the exit port; and the exit port on the distal end of the housing for delivering the aerosol to a patient in need of aerosolized active agent.

In accordance with an exemplary embodiment, an aerosol delivery system, comprises: an aerosol generator for producing an aerosol; a positive pressure generator for producing a pressurized ventilation gas; in one example, a splitter for splitting the pressurized ventilation gas into a carrier gas and a ventilation gas and a conduit from the positive pressure generator to the splitter; an aerosol transition adapter arranged to combine the aerosol produced by the aerosol generator with the carrier gas from the splitter, and wherein the transition adapter divides the carrier gas into a plurality of streams of carrier gas, which are directed to at least partially encircle and to flow in parallel with the aerosol entering the transition adapter, and which forms an entrained aerosol; an aerosol delivery connector having a port for receiving the entrained aerosol, a port for entry of the ventilation gas, a patient-aerosol interface port for delivering the entrained aerosol from the aerosol transition adapter and the ventilation gas from the splitter to a patient, and a port for exit of expiration gas from the patient; and a patient interface for receiving the entrained aerosol and the ventilation gas from the aerosol delivery connector.

In accordance with an exemplary embodiment, a method of producing an entrained aerosol comprises: generating an aerosol; providing a source of carrier gas from a ventilator; and combining the aerosol and the carrier gas by dividing the carrier gas into a plurality of streams of carrier gas, which are at least partially encircling and in parallel with the aerosol to form an entrained aerosol.

BRIEF DESCRIPTION OF THE DRAWINGS

The disclosure is explained below with reference to the exemplary embodiments shown in the drawings. In the drawings.

DETAILED DESCRIPTION

Figure 2:
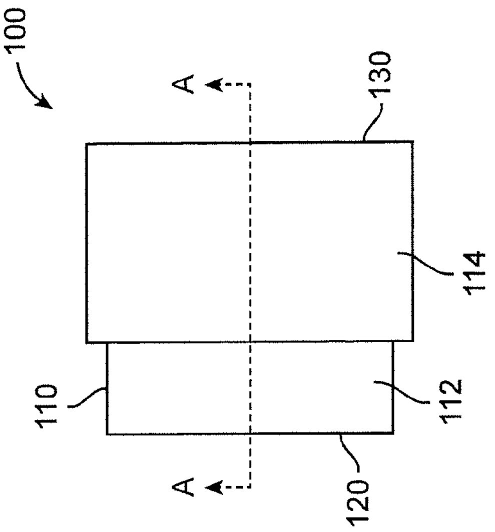
FIG. 2 is a side view of the transition adapter as shown in FIG. 1 in accordance with an exemplary embodiment.

Aerosols are useful in drug delivery. For example, it is often desirable to treat respiratory ailments with, or deliver drugs by means of, aerosol sprays of fine, dispersed particles of liquid and/or solid, e.g., powder, medicaments, etc., which are inhaled and delivered into a patient's lungs. Aerosols can be generated by a heated capillary aerosol generator (CAG) by feeding a liquid formulation into a heated capillary tube or passage (referred to herein as "heated capillary") while heating the capillary sufficiently such that the liquid formulation is at least partially volatilized, so that upon discharge from the heated capillary, the liquid formulation is in the form of an aerosol. The length of the capillary can depend on heat requirements dictated by, among other factors, the composition of the aerosol to be generated.

As used herein, the term "aerosol" refers to liquid or solid particles that are suspended in a gas. The "aerosol" or "aerosolized agent" referred to herein contains one or more of the active agents, as referred to above.

The term "ventilation" or "respiratory ventilation" as used herein refers to mechanical or artificial support of a patient's breathing. The overall goals of mechanical ventilation are to optimize gas exchange, patient work of breathing and patient comfort while minimizing ventilator-induced lung injury. Mechanical ventilation can be delivered via positive-pressure breaths or negative-pressure breaths. Additionally, the positive-pressure breaths can be delivered noninvasively or invasively. Noninvasive mechanical ventilation (NIMV) generally refers to the use of a mask or nasal prongs to provide ventilatory support through a patient's nose and/or mouth. The most commonly used interfaces for noninvasive positive pressure ventilation are nasal prongs, nasopharyngeal tubes, masks, or nasal masks. NIMV can be distinguished from those invasive mechanical ventilatory techniques that bypass the patient's upper airway with an artificial airway (endotracheal tube, laryngeal mask airway or tracheostomy tube). NIMV can be provided by either bi-level pressure support (so called "BI-PAP") or continuous positive airway pressure (CPAP).

The employment of mechanical ventilation, whether invasive or non-invasive, involves the use of various respiratory gases, as would be appreciated by the skilled artisan. Respiratory gases are sometimes referred to herein as "CPAP gas," "ventilation gas," "ventilation air," "inspiratory flow," expiratory flow," or simply "air." As used herein, the terms "ventilation gas", "air", "oxygen", "medicinal gas" and "gas" are used interchangeably to refer to a ventilation gas or flow driven oxygen/air and include any type of gas normally used for respiratory therapy. The term "ventilator" referred to herein can also be described as an oxygen/air mixing flow driver as the pressurized oxygen and air are mixed and provide the source of ventilation gas. A carrier gas is used to carry aerosolized drugs in administering respiratory therapy. The term "carrier gas" can be used herein interchangeably with the term "entrainment gas" and includes any type of gas normally used for respiratory therapy as disclosed above.

A ventilation circuit for administering positive pressure ventilation includes a positive pressure generator or a source of positive end expiratory pressure (PEEP valve or column of water) connected by tubing to a patient interface, such as a mask, nasal prongs, or an endotracheal tube, and an exhalation path, such as tubing that allows discharge of the expired gases, for example, to the ventilator such as a constant flow CPAP or to an underwater receptacle as for "bubble" CPAP. The inspiratory and expiratory tubes can be connected to the patient interface via a "Y" connector or an aerosol delivery connector, for example, as disclosed in WO 2009/117422A2, which contains a port for attaching each of the inspiratory and expiratory tubes, as well as a port for the aerosol, the patient interface and, a port for attaching a pressure sensor.

The aerosol generated by the capillary or other means is known to be mixed with a carrier gas or sheath gas for transporting to the patient. Admixing the aerosol and the heated sheath gas in a transition adapter is disclosed, for example, in U.S. Patent Publication No. 2008/0110458, which is incorporated herein by reference in its entirety, wherein the sheath gas is heated to about 125° C. to 145° C. and is introduced into the transition adapter through a cavity that is perpendicular to the main direction of the aerosol flow entering the transition adapter (as shown in FIG. 16 of U.S. Patent Publication No. 2008/0110458). The admixed gas and aerosol impacts the transition adapter's spherical surface before the aerosol is entrained in the aerosol tube. Due to this aerosol impaction, lost drug is directed to a fluid trap as large aerosol particles are removed from the aerosol stream. The present disclosure provides that the introduction of the carrier gas at a lower temperature and in parallel to the main direction of the aerosol flow such that as the carrier gas surrounds and is combined with the aerosol in a much less turbulent pattern minimizes drug loss. The geometry of the inner cavity of the transition adapter resembles the geometry of the aerosol plume exiting the heated capillary and includes a cone and a cylinder, wherein at a distal end of the inner cavity, the cone's diameter is larger than the diameter of the widest portion of the aerosol plume so that the aerosol impaction is minimized.

In accordance with an exemplary embodiment, the transition adapter's less turbulent pattern of carrier gas flow results from the division of the carrier gas into a plurality of the carrier gas streams entering the cone of the transition adapter in parallel and co-directionally with the main direction of the flow of aerosol entering the transition adapter after being generated by the aerosol generator. In accordance with an exemplary embodiment, the source of the carrier gas can be any source of gas suitable for delivery of pulmonary therapy and pulmonary therapy drugs.

In an exemplary embodiment, the source of the carrier gas is a ventilator, which is used for providing ventilator support to the patient receiving aerosolized drug. For example, in an exemplary embodiment, the flow of the ventilator's inspiratory gas is split into a plurality of sub-flows using a splitter such that at least one sub-flow continues to be used for ventilation purposes, such as, for example, providing positive end expiratory pressure (PEEP) in CPAP ventilation and at least one sub-flow is used as a carrier gas for delivering aerosol to the patient.

The transition adapter will now be disclosed in more detail with references to FIGS. 1-6C and 9A-12E, which represent exemplary embodiments of the transition adapter.

Figure 1:
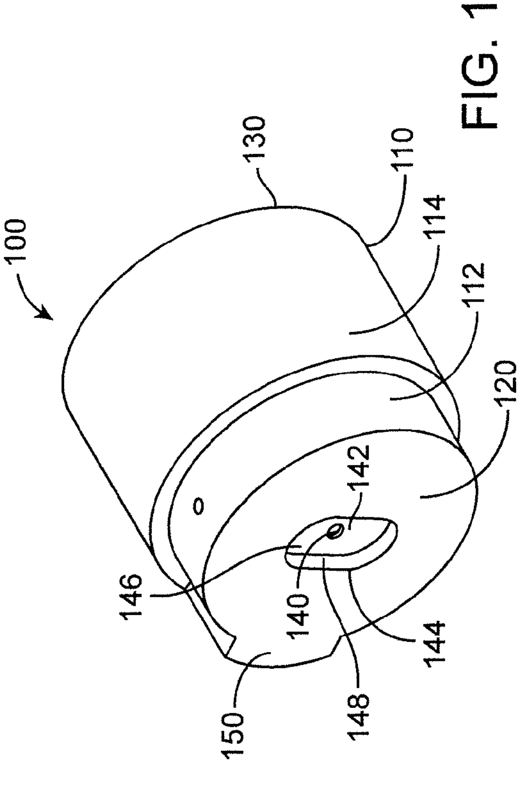
FIG. 1 is a perspective view of a transition adapter in accordance with an exemplary embodiment.

FIG. 1 is a perspective view of an aerosol transition adapter 100 in accordance with an exemplary embodiment. As shown in FIG. 1, the transition adapter 100 includes a housing 110 having a proximal end 120 and a distal end 130. The proximal end 120 has an aerosol passage 140 for receiving an aerosol 234 produced by a heated capillary 232 (see FIGS. 7A-7B) of an aerosol generator 230 (see FIGS. 7A-7B). The aerosol passage 140 preferably includes a coupling port 142, which contains a connection to a distal end (see FIGS. 7A-7B) of the heated capillary 232. The aerosol 234 enters into an inner cavity 170 (see FIG. 3) within the transition adapter 100 through the aerosol passage 140 where the aerosol 234 is at least partially encircled and carried forward by parallel streams of carrier gas 316, which are originated from a source of gas or ventilator 300 and introduced into the transition adapter through at least one gas entry port 154, or alternatively, a plurality of gas entry ports 154 (see FIGS. 3 and 6) to form an entrained aerosol 240 (see FIGS. 7A-7B) which is a combination of the aerosol 234 and the carrier gas 316. In accordance with an exemplary embodiment, the source of gas 300 (see FIGS. 7A-7B) is a continuous positive airway pressure (CPAP) ventilator, which produces inspiratory flow 302 and receives filtered expiratory flow 362 (see FIGS. 7A-7B).

As shown in FIG. 1, the aerosol passage 140 has a coupling port 142, which receives the distal end of the heated capillary 232 of the aerosol generator 230, which is positioned within an oval cavity 144 on the proximal end 120 of the housing 110. In accordance with an exemplary embodiment, the cavity 144 (which can have any shape, for example, oval, round, rectangular or square; only the oval shape is shown in FIG. 1) preferably has an end wall 146 and side walls 148, which are configured to provide a secure method of coupling the distal end of the aerosol generator 230 to the coupling port 142 of the aerosol passage 140. The aerosol passage 140 is in communication with the inner cavity 170 (see FIG. 3) of the transition adapter 100.

The housing 110 preferably includes a generally cylindrical proximal portion 112, a cylindrical distal portion 114, and a carrier gas connection port 150 (see FIG. 3) extending perpendicular to the proximal end 120 and configured to receive a carrier gas line 314 (see FIGS. 7A-7B), which transports a stream of carrier gas 316 (see FIGS. 7A-7B) from the ventilator 300 to the transition adapter 100.

FIG. 2 is a side view of the transition adapter 100 as shown in FIG. 1 in accordance with an exemplary embodiment. As shown in FIG. 2, the housing 110 of the transition adapter 100 has a cylindrical proximal portion 112 and a cylindrical distal portion 114, which extend from the proximal end 120 to the distal end 130 of the housing 110. In accordance with an exemplary embodiment, an outer diameter of the cylindrical proximal portion 112 is smaller than an outer diameter of the cylindrical distal portion 114.

Figure 3:
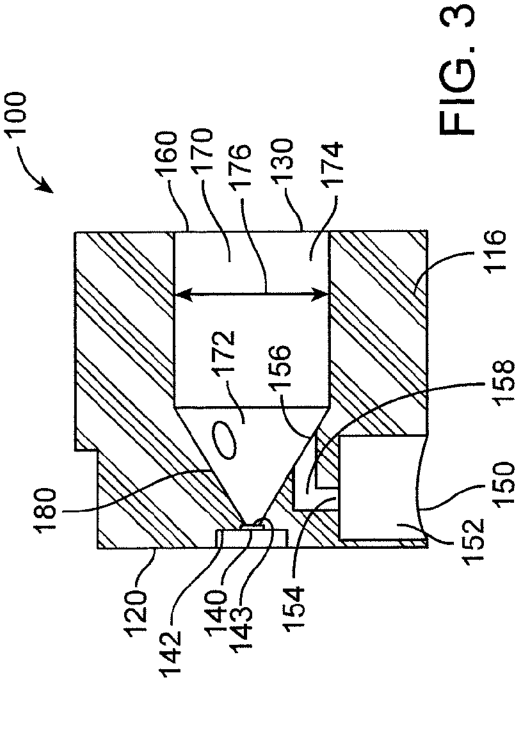
FIG. 3 is a cross-sectional view of the transition adapter as shown in FIG. 1 along the line A-A of FIG. 2.
Figure 7A:
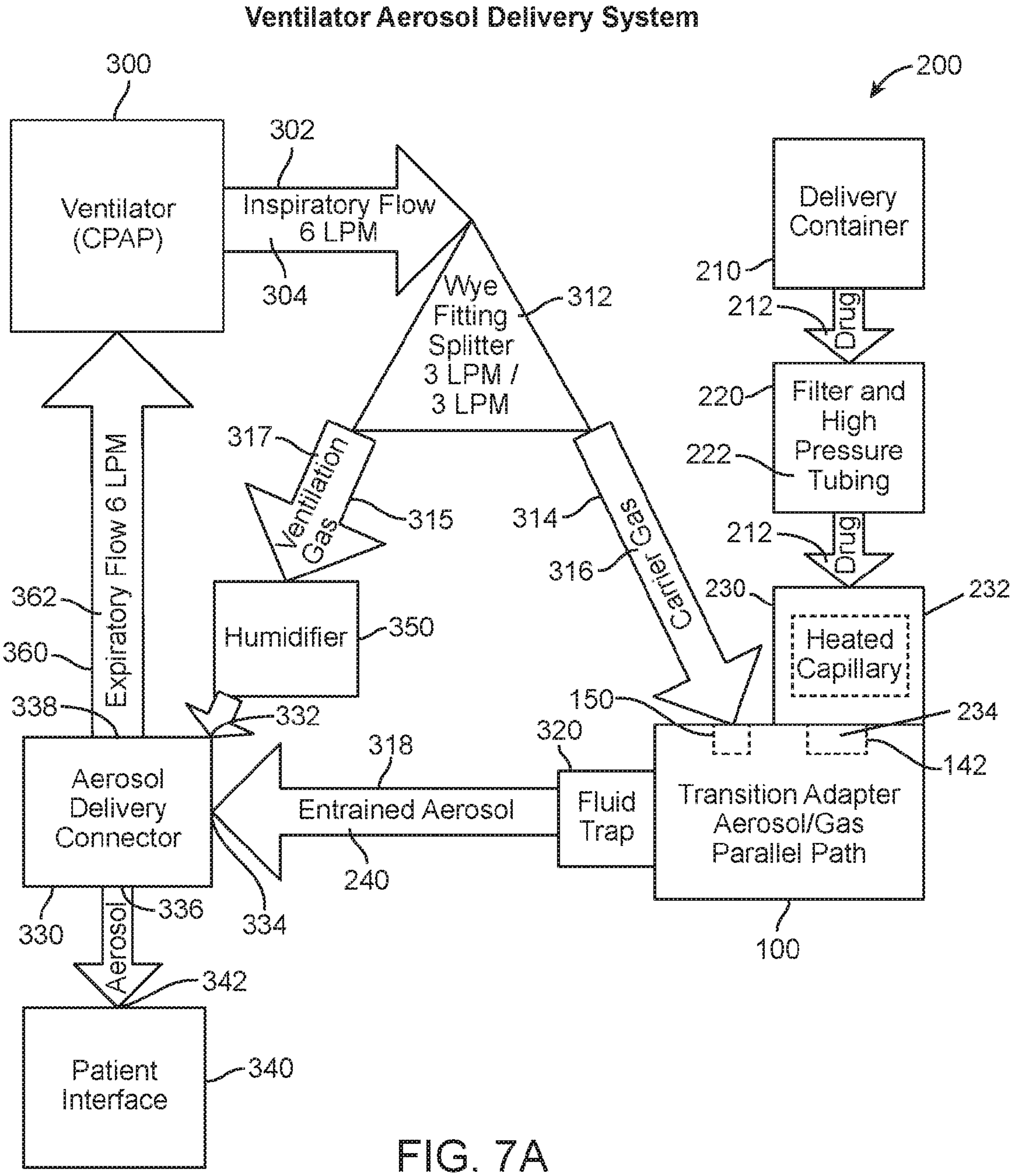
FIG. 7A is a block diagram of a ventilator aerosol delivery system for a continuous positive airway pressure ("CPAP") system in accordance with an exemplary embodiment.
Figure 7B:
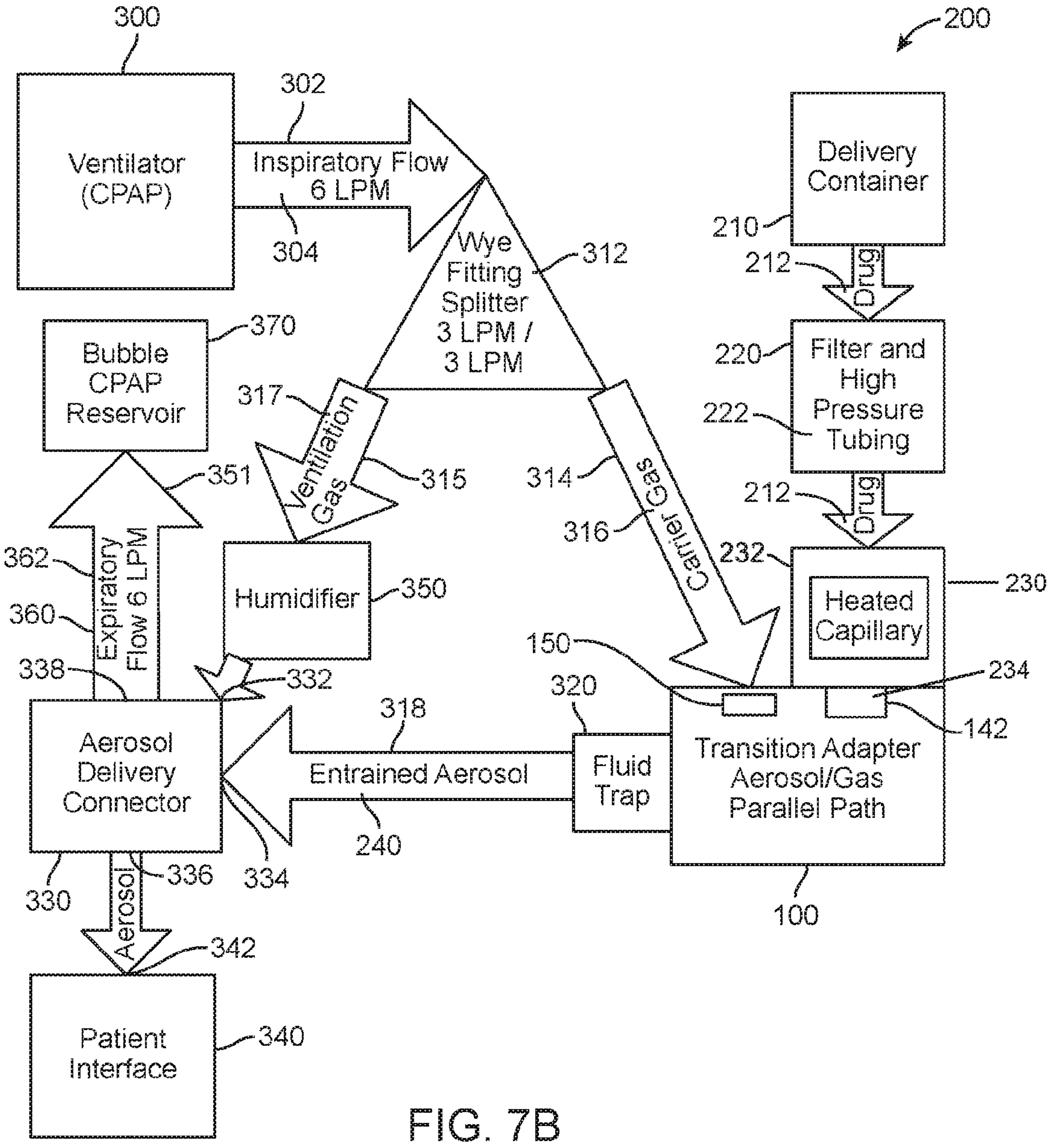
FIG. 7B is a block diagram of a ventilator aerosol delivery system for a bubble CPAP in accordance with an exemplary embodiment.

FIG. 3 is a cross-sectional view of the transition adapter 100 as shown in FIG. 1 along the line A-A of FIG. 2. As shown in FIG. 3, the housing 110 of the transition adapter 100 includes a cylindrical body 116, which includes a carrier gas connection port 150 for receiving the carrier gas 316 via a carrier gas line 314 from a ventilator 300 (FIGS. 7A-7B). The carrier gas connection port 150 has a cylindrical cross-section 152, which is in communication with a plurality of gas entry ports 154 and a plurality of corresponding gas exit ports 156 via a passage 158. Each of the gas exit ports 156 delivers a stream of carrier gas 316 to the inner cavity 170 of the transition adapter 100.

In accordance with another exemplary embodiment as shown in FIGS. 12A-12E, the source of gas 300 can be introduced into the inner cavity 170 via a single gas entry port 154 and a single gas passage 158. In accordance with an exemplary embodiment, rather than multiple or a plurality of passages or conduits 158 for introducing the gas stream 300 into cavity 170, the separation of gas streams 300 into the inner cavity 170 can be performed through a plurality of openings or exit ports 156 along the conical section 180.

As shown in FIG. 3, the aerosol passage 140 is in communication with the inner cavity 170 which receives the aerosol 234 from the heated capillary 232 and the streams of carrier gas 316 from the plurality of gas exit ports 156 and directs the streams of carrier gas 316 to flow in parallel with the main direction of the flow of aerosol 234. The carrier gas streams 316 at least partially encircle the aerosol flow path within the inner cavity and carry the aerosol 234 toward the distal end 130 such that the entrained aerosol 240 is created within the inner cavity. The entrained aerosol exits the transition adapter 100 through an exit port 160 at the distal end 130 and flows into an aerosol tube 318 (see FIGS. 7A-7B).

As shown in FIG. 3, the inner cavity 170 has a proximal portion 172 having a conical section 180, which expands outward from the aerosol passage 140 towards the distal end 130 of the housing 110. In accordance with an exemplary embodiment, the walls of the conical section 180 of the proximal portion 172 of the inner cavity 170 form an angle of approximately 45 degrees to approximately 75 degrees (for example, an approximately 60 degree cone). In accordance with an exemplary embodiment, the distal portion 174 of the inner cavity 170 can have a slightly tapered inner diameter. In accordance with an exemplary embodiment, the plurality of corresponding gas exit ports 156 are positioned within the proximal portion 172 of the inner cavity 170 along the conical section 180.

In accordance with an exemplary embodiment, the plurality of gas entry ports 154 for receiving the carrier gas 316 from the ventilator 300 has at least two entry ports 154 (FIG. 6C), and preferably at least three entry ports 154 (FIG. 6A) or more (see, for example FIG. 6B) and thereby splitting the carrier gas in a plurality of carrier gas streams. From each of the entry ports 154, a stream of carrier gas is further directed to a corresponding number of gas exit ports 156, which are located within the conical section 180 of the inner cavity 170. In accordance with an exemplary embodiment, each of the gas exit ports 156 delivers a plurality of streams of carrier gas such that they at least partially encircle and flow in parallel to the main flow of aerosol 234 delivered from the aerosol passage 140. Since the aerosol may have a plume with sprays angling from the main direction toward the exit from the transition adapter, the term "main flow of aerosol" is used to indicate the direction along which carrier gas 316 will be flowing. In accordance with an exemplary embodiment, the plurality of gas exit ports 156 are placed at a distance from the aerosol passage 140 in a pattern that allows the plurality of carrier gas streams to at least partially encircle the flow of the aerosol 234 after the aerosol has entered the conical section 180 and has passed the gas exit ports 156. For example, for a plurality of exit ports 156, which are three in number, each of the three exit ports 156 are separated approximately 120 degrees from one another around the aerosol passage 140.

In accordance with an exemplary embodiment, each of the plurality of exit ports 156 are approximately 1 to 10 millimeters in diameter and located at an approximately 3 to 20 millimeter radius from a central axially extending aerosol passage 143 from which the aerosol 234 enters the housing 110 of the transition adapter 100. The exit port 160 at the distal end 174 of the transition adapter 100 forms a flow channel having an inner diameter 176, for example, of approximately 22 mm to 50 mm.

Figure 4:
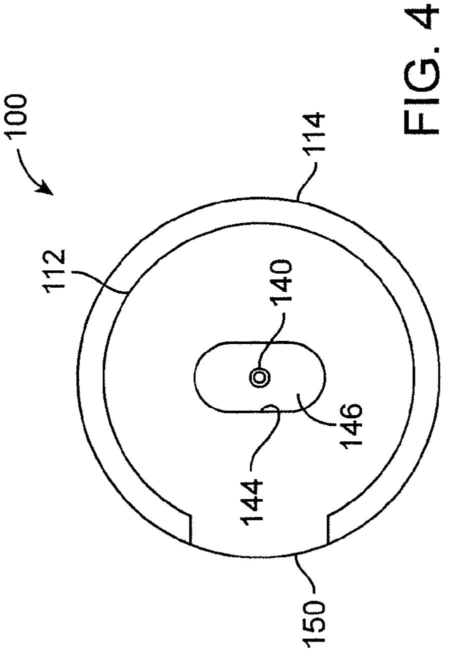
FIG. 4 is an end view of the transition adapter as shown in FIG. 1 in accordance with an exemplary embodiment.

FIG. 4 is an end view of the proximal end 120 of the transition adapter 100 as shown in FIG. 1 in accordance with an exemplary embodiment. As shown in FIG. 4, the proximal end 120 of the transition adapter 100 includes an aerosol passage 140, which is housed within a cavity 144 having a round, oval or other suitable shape to receive a distal end of the heated capillary 232 housed within an aerosol generator 230.

Figure 5A:
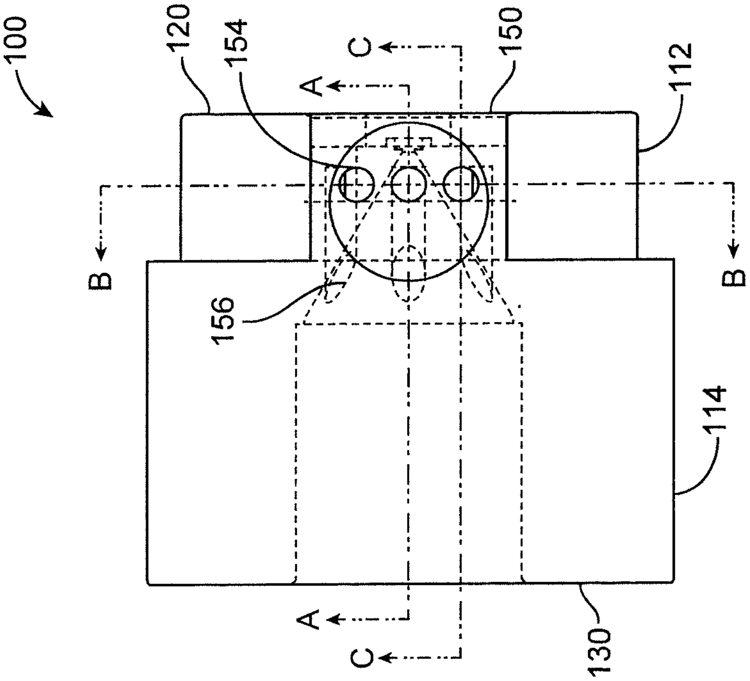
FIG. 5A is a side view of the transition adapter as shown in FIG. 1.

FIG. 5A is a side view of the transition adapter 100 as shown in FIG. 1 showing the gas connection port 150 in accordance with an exemplary embodiment. As shown in FIG. 5A, the carrier gas connection port 150 is configured to receive a carrier gas line 314 from a ventilator 300. The carrier gas connection port 150 has a cylindrical cross-section 152 and a plurality of gas entry ports 154, each of which is in communication with corresponding exit ports 156. Each of the exit ports 156 delivers a stream of carrier gas to the inner cavity 170 of the transition adapter 100. For example, as shown in FIG. 5A, the plurality of gas entry ports 154 can be three (3) in number and can be located relative to one another in a vertical or straight line within the carrier gas connection port 150.

Figure 5B:
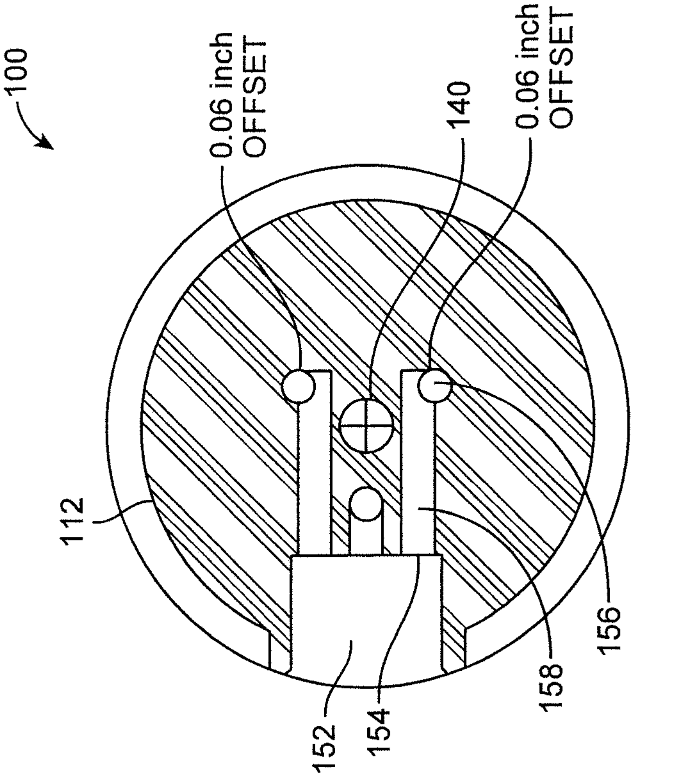
FIG. 5B is a cross-sectional view of the transition adapter as shown in FIG. 5A along the line B-B.

FIG. 5B is a cross-sectional view of the transition adapter 100 as shown in FIG. 5A along the line B-B. As shown in FIG. 5B, each of the plurality of gas entry ports 154 are in communication with a corresponding exit port 156 via a passage 158. The passages 158 extend from the gas entry port 154 to a corresponding gas exit port 156. In accordance with an exemplary embodiment, the passages 158 are cylindrical and extend inward from the carrier gas connection port 150. In accordance with an exemplary embodiment, two of the three exit ports 156 are slightly offset from a distal end of the corresponding passages 158 (for example, approximately 0.06 inches). The offsetting of two of the three exit ports 156 allows for the exit ports 156 to be equally spaced around the aerosol passage 140 as the aerosol passage 140 enters the inner cavity 170 of the transition adapter 100. In addition, the plurality of gas exit ports 156 can be positioned within the proximal portion of the inner cavity 170 at an equidistance from the aerosol passage 140.

Figure 5D:
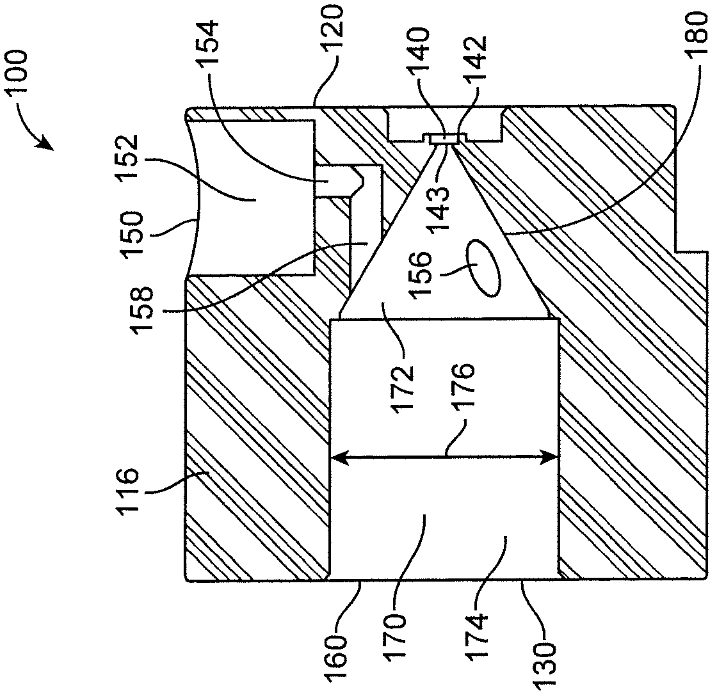
FIG. 5D is a cross-sectional view of the transition adapter as shown in FIG. 5A along the line A-A.
Figure 5C:
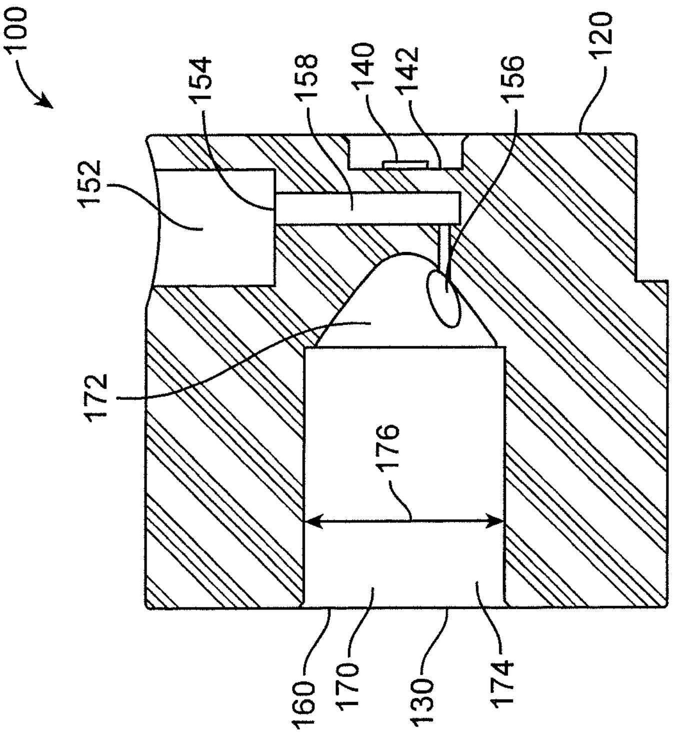
FIG. 5C is a cross-sectional view of the transition adapter as shown in FIG. 5A along the line C-C.

FIG. 5C is a cross-sectional view of the transition adapter 100 as shown in FIG. 5A along the line C-C. As shown in FIG. 5C, each of the passages 158 can extend inward from the carrier gas connection port 150 towards the aerosol passage 140 and then each of the passages 158 transition towards the inner cavity 170. Each of the passages 158 has a proximal portion extending from the entry port 154 to the transition, and a distal portion, which extends from the transition to the exit port 156. The transition of the passage 158 from the proximal portion to the distal portion can be at a right angle to one another, or alternatively, the transition can be rounded or have a curvature thereto.

As shown in FIG. 5C, the inner cavity 170 has a proximal portion 172 having a conical section, which expands outward from the aerosol passage 140 towards the distal end 130 of the housing 110. In accordance with an exemplary embodiment, the distal portion 174 of the inner cavity 170 has a slightly tapered inner diameter. In accordance with an exemplary embodiment, the plurality of corresponding gas exit ports 156 are positioned within the proximal portion 172 of the inner cavity 170.

FIG. 5D is a cross-sectional view of the transition adapter as shown in FIG. 5A along the line A-A. As shown in FIG. 5D, the passages 158 can extend inward from the carrier gas connection port 150 towards the aerosol passage 140 and then transitions toward the inner cavity 170.

Figure 6A:
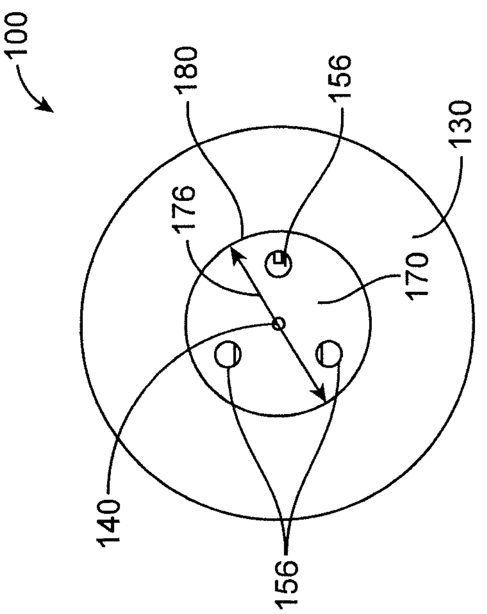
FIG. 6A is an end view of the transition adapter as shown in FIG. 1 in accordance with an exemplary embodiment.
Figure 6B:
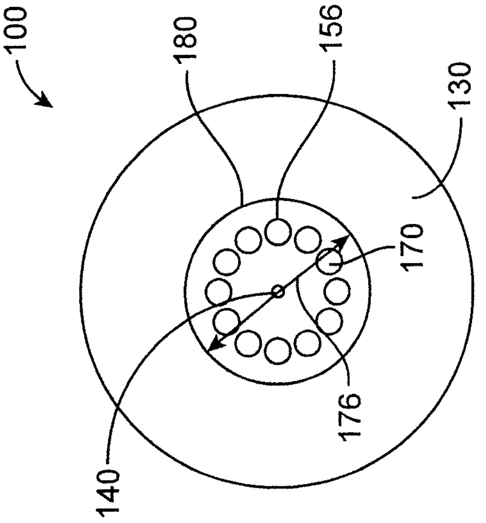
FIG. 6B is an end view of the transition adapter as shown in FIG. 1 in accordance with an exemplary embodiment.
Figure 6C:
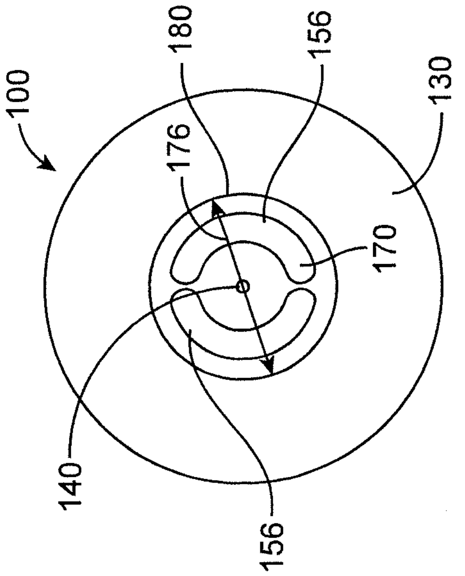
FIG. 6C is an end view of the transition adapter as shown in FIG. 1 in accordance with an exemplary embodiment.

FIGS. 6A, 6B, and 6C are the end views of the distal end 130 of the transition adapter 100 as shown in FIG. 1. As shown in FIG. 6A, the distal end 130 of the transition adapter 100 has a uniform inner diameter 176 (see also FIG. 3). In accordance with an exemplary embodiment, the plurality of exit ports 156 is positioned within the proximal portion 172 of the inner cavity 170 along the conical portion 180. In accordance with an exemplary embodiment, the plurality of gas entry ports 154 for receiving the stream of carrier gas 316 from the ventilator 300 has at least three entry ports 154, each of the at least three entry ports 154 directing a stream of gas 316 to a corresponding gas exit port 156, which is located within the conical portion 180 of the inner cavity 170. In accordance with an exemplary embodiment, the plurality of gas exit ports 156 are positioned within the proximal portion of the inner cavity 170 at an equidistance from the aerosol passage.

FIG. 6B shows another embodiment of the transition adapter 100 with more than two gas exit ports 156. As shown in FIG. 6B, the plurality of gas exit ports 156 can include a plurality of exit ports 156, which form an outer ring around the aerosol passage 140. FIG. 6C shows an exemplary embodiment wherein the plurality of exit ports 156 includes two exit ports 156, which form an outer ring having two or more sections thereto. Each of the two or more sections forms a portion of the outer ring, which surrounds the aerosol passage 140.

In accordance with an exemplary embodiment, within the aerosol delivery system 200 (FIGS. 7A-7B), this example shows that there can be a critical balance of the ventilation gas flow 317 and the carrier gas flow 316 after they are split. From the splitter 312, the ventilation gas 317 flows through the ventilation gas tube 315 into the aerosol delivery connector 330 at the ventilation port 332 and the aerosol 342 exits the aerosol delivery connector 330 at the patient port 336 and enters the patient interface 340 directly or through optional tubing or conduit 344. The carrier gas 316 flows from the splitter 312 through the carrier gas tube 314 into the transition adapter 100. Within the transition adapter 100, the carrier gas 316 is divided as it passes through the exit ports 156 into the inner cavity 170 in the form of parallel pathways or flows (for example, ranged from 3 up to 50 in number) and carries the aerosol along the length of the transition adapter 100, thereby forming the entrained aerosol 240. The entrained aerosol exits the transition adapter 100 and enters the entrained aerosol tube 318 before entering the aerosol delivery connector 330 at the aerosol port 334. In accordance with an exemplary embodiment, resistance to flow of the carrier gas 316 can be created in the transition adapter 100 by the division into smaller flows and the selection of sizes of the parallel flows (driven by the size of exit ports 156) within the transition adapter 100. For example, selecting a larger diameter of parallel flows or larger numbers of flows can provide less resistance when compared to a single flow or to several flows with smaller diameters. In an exemplary embodiment, one important feature is that the geometry of the exit ports does not significantly contribute to the resistance increase in the carrier gas flow, and assures optimal aerosol entrainment. The ventilator's inspiratory flow 304 is operated under a range of pressures, for example, between approximately 5 and 50 cm $H_2O$. An increase of flow resistance of carrier gas 316 within the transition adapter 100 may influence the inspiratory flow 304 gas pressure and thus interfere with patient ventilation.

In accordance with an exemplary embodiment, the ventilator aerosol delivery system 200 is disclosed in which inspiratory flow 304 is split into separate sub-flows, such that one sub-flow is used as a carrier gas 316 for the aerosol and is directed into the transition adapter 100 and another sub-flow is used as a ventilation gas 317. For example, currently, a common ventilator aerosol delivery system is a closed ventilation system in which the volume of gas produced by the ventilator travels to a patient who is receiving mechanical ventilation and back to the ventilator. Introducing gas from a separate source into this closed ventilation system (such as a carrier gas for administering pulmonary medication) may not be desirable since the inspiratory flow increases and thereby creates an imbalance of flows within the closed ventilation system. Accordingly, it would be desirable to split the inspiratory flow 304 that originates from the ventilator 300 and using one portion of the inspiratory flow 304 as a carrier gas 316. The ventilator aerosol delivery system 200 as disclosed herein can also be used in open ventilation circuits such as bubble CPAP (see FIG. 7B).

FIG. 7A is a block diagram of an aerosol delivery system 200 in accordance with an exemplary embodiment. The aerosol delivery system 200 includes an aerosol generator 230, a source of liquid material or liquid formulation 212 flowing through the aerosol generator 230, a transition adapter 100, a ventilator 300, an aerosol delivery connector 330, and a patient interface 340. In accordance with an exemplary embodiment, the aerosol delivery system 200 as shown in FIG. 7A, delivers inspiratory flow 304 via the inspiratory limb 302 from the ventilator 300. In addition, to account for the heat of the aerosol produced by the aerosol generator 230, the system 200 can limit the temperature of the entrained aerosol 240 by optimizing the length of an entrained aerosol tube 318, which delivers the entrained aerosol 240 from the transition adapter 100 to the aerosol delivery connector 330.

Pursuant to this disclosure, the delivery of the inspiratory flow 304 via the inspiratory limb 302 of the ventilator's circuit allows the ventilator 300 to control the inspiratory flow levels. For example, in accordance with an exemplary embodiment, a flow of approximately 3 liters per minute (LPM) of ventilation gas 317 can be split off from the approximately 6 liters per minute (LPM) inspiratory flow 304 from the ventilator 300 using a splitter 312 in a form, for example, of a T-fitting or a Y ("Wye") fitting. The volumes of gas divided by the splitter 312 can be in equal or unequal portions to the initial volume of gas produced by the ventilator 300. By diverting the part of the inspiratory flow 304 and using it to deliver the entrained aerosol 240 to the patient, the flow rate of the entrained aerosol 240 is reduced from approximately 6 liters per minute to approximately 3 liters per minute, providing a less turbulent flow pattern.

Figure 7C:
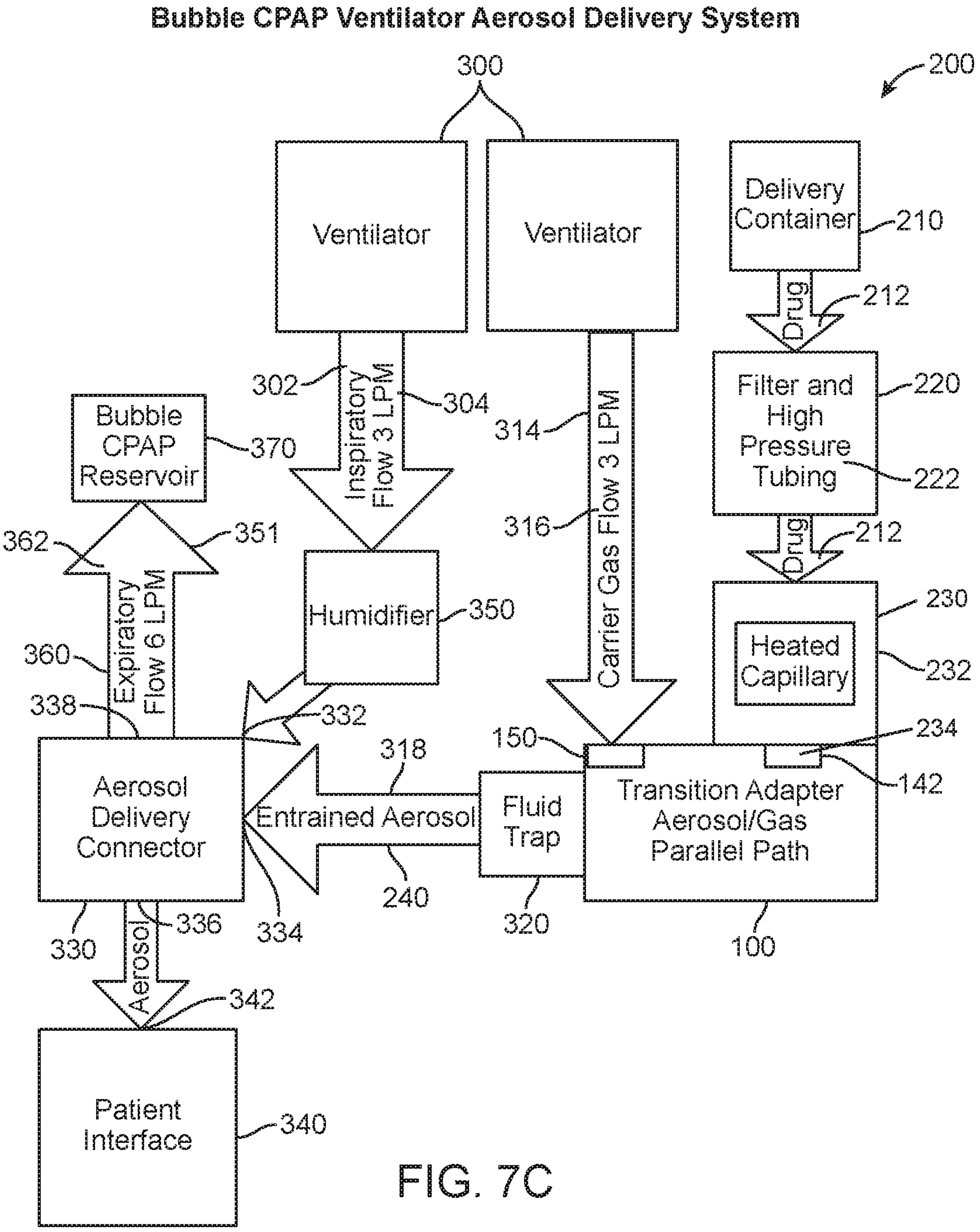
FIG. 7C is a block diagram of a ventilator aerosol delivery system for a bubble CPAP in accordance with an exemplary embodiment in which two independent sources of ventilation are being used.

In an exemplary embodiment, the splitter 312 is not used and the requisite volume of ventilation gas 317 and carrier gas 316 are being provided by separate sources as shown in FIG. 7C. In other words, the original flow of approximately 6 liters per minute of the oxygen and air is split into two separate oxygen and air source lines that are supplied by two separate ventilators. The flow of approximately 3 liters per minute (LPM) of ventilation gas 317 is separately generated by a ventilator 300 and a second ventilator 300 generates approximately 3 liters per minute (LPM) inspiratory flow 304. In accordance with an exemplary embodiment, aerosol losses are minimized since impaction is decreased with the less turbulent flow pattern within the transition adapter 100. For example, a more concentrated entrained aerosol 240 flowing at a flow rate of approximately 3 liters per minute at the patient interface is close to the expected peak inspiratory flow produced by the patient and thus more drug is directed to the patient. In accordance with an exemplary embodiment, pursuant to the current standard of care, the aerosol is being added into the approximately 6 liters per minute inspiratory flow which exceeds the expected peak inspiratory flow. Thus, the amount of aerosolized drug per unit volume directed to the patient is less than described in this disclosure. The carrier gas 316 combines with the aerosol in the transition adapter 100 and the resulting entrained aerosol 240 is directed to the patient interface 340 via an aerosol port 336 of the aerosol delivery connector 330. The other approximately 3 liters per minute (LPM) of inspiratory flow 304 is the ventilation gas flow 317. In an exemplary embodiment, the ventilation gas flow enters the aerosol delivery connector at a ventilation port 332, for a total flow of approximately 6 liters per minute (LPM), initially produced by the ventilator 300, which is available for patient inspiration. In addition, by accounting for the total output of the inspiratory flow from the ventilator 300, the system 200 avoids triggering an alarm, which can sound due to unaccounted and/or excess flow of gas returned to the ventilator 300 upon exhalation. It should be understood that the values for the inspiratory flow, carrier gas flow, ventilation gas flow and entrained aerosol flow are given herein as exemplary and can be modified and apportioned as needed to accommodate a particular patient or system.

In accordance with an exemplary embodiment as shown in FIG. 7A, the aerosol 234 is produced from a drug delivery container 210, which includes a liquid formulation 212, such as, for example, a pulmonary surfactant Surfaxin® (lucinactant) marketed by Discovery Laboratories, Inc. For example, the liquid formulation 212 can include a lung surfactant or any other drug preparation adapted for delivery as an aerosol to an infant's lungs or a medicament to treat Respiratory Distress Syndrome (RDS) in infants or any other disease in children and adults. The liquid formulation 212 can be contained within a dose container, such as, for example, a syringe, which can be pre-portioned.

In accordance with an exemplary embodiment, the liquid formulation 212 is prepared by initially heating the dose container on a hot plate/stirrer to liquefy the formulation to a desired viscosity for delivery to the aerosol generator 230. The aerosol delivery system 200 is configured to supply the liquid formulation 212 from the dose container at a constant and continuous rate to the heated capillary 232 of the aerosol generator 230, wherein the liquid formulation 212 is at least partially volatized. Alternatively, the liquid formulation 212 is prepared by reconstituting a solid formulation (e.g., freeze-dried pharmaceutical formulation) with an appropriate pharmaceutically acceptable carrier such as, for example, water, buffer or saline solution and optionally heated. Alternatively, multiple liquid formulations 212 containing different drugs or reservoirs containing auxiliary substances other than drugs, for example, pharmaceutically acceptable carriers together with multiple feeding lines, can be provided as needed.

The liquid formulation 212 is delivered via a flow line 220 in the form of a filter and high pressure tubing arrangement 222 to an inlet of the heated capillary 232 of the aerosol generator 230. Alternatively, the feed line 220 in the form of a filter and high pressure tubing arrangement 222 can be eliminated and the liquid formulation 212 can be connected directly with the aerosol generator 230.

The aerosol generator 230 can include a pair of electrical leads (not shown), which transfer power from a power source to a heater, which transfers heat to the heated capillary 232 of the aerosol generator 230 and heats the heated capillary 232 to a temperature sufficient to at least partially volatilize the liquid formulation 212 that is introduced to the heated capillary 232. For example, the at least partially volatilized liquid formulation 212 can be driven through a restrictor to atomize the liquid material or formulation 212. The liquid material is preferably introduced into the heated capillary 232 through an inlet of the heated capillary 232 connected to a source of liquid material. The at least partially volatilized material, the aerosol 234 is driven out of the heated capillary 232 through the outlet of the heated capillary, for example, the back pressure of the liquid from the source of liquid formulation 212 causes the liquid to be ejected from the outlet. Alternatively, the system 200 can include a heater block in thermal contact with the heated capillary 232. The heater block can include an upper assembly and a lower assembly, which encases the heated capillary 232 to produce an aerosol 234, for example, as disclosed in U.S. Patent Publication No. 2008/0110458, which is incorporated herein by reference in its entirety.

In accordance with an exemplary embodiment, the heated capillary is a tipped capillary as disclosed in U.S. Pat. No. 7,500,479, the contents of which are hereby incorporated by reference in their entirety. For example, as disclosed in U.S. Pat. No. 7,500,479, the heated capillary can include a constriction in the form of a domed (restricted) capillary end or formed tip at the outlet or distal end of the flow passage. The aerosol generator 230 can be a soft-mist generator as disclosed in U.S. Pat. Nos. 5,743,251 and 7,040,314. Alternatively, the aerosol generator 230 can be an ultrasonic nebulizer or vibrating membrane nebulizer or vibrating screen nebulizer. In one embodiment, the aerosol generator 230 is Aeroneb® Professional Nebulizer (Aerogen Inc., Mountain View, Calif., USA). Alternatively, the aerosol generator 230 may be a metered dose inhaler, a liquid dose instillation device, or a dry powder inhaler as disclosed in U.S. Patent Publication No. 2012/0003318, which is incorporated herein by reference in its entirety. Also, one or more aerosol generators 230 can be used.

As shown in FIG. 7A, the aerosol 234 exits from the heated capillary 232 into the transition adapter 100. In addition to receiving the aerosol 234, the transition adapter 100 also receives carrier gas 316, which is introduced as a plurality of separate streams of the carrier gas 316 flowing in parallel with the main flow of the aerosol 234. The plurality of separate streams of the carrier gas 316 carries the aerosol 234 within the transition adapter 100 and out of the transition adapter 100 in a form of an entrained aerosol 240.

As disclosed above, the transition adapter 100 includes a housing 110 and a plurality of entry ports 154 for receiving a plurality of streams of carrier gas 316, which exit through a corresponding exit port 156 in parallel with the main direction of the generated aerosol 234 to produce an entrained aerosol 240. Due to at least the configuration of the transition adapter 100 including (i) the geometry of the transition adapter 100 and (ii) the arrangement of the ports 254, 256 for the aerosol 234 and the plurality of streams of carrier gas within the transition adapter 100, two or more streams of carrier gas 316 flowing in parallel with the main direction of the aerosol flow 234 at least partially encircle the aerosol flow 234 and carry the thus formed entrained aerosol 240 through and out of the transition adapter 100 into an entrained aerosol tube 318. Such configuration of the transition adapter 100 minimizes the amount of aerosol 234 impaction on the side walls of the transition adapter 100 and on the connecting aerosol delivery components or entrained aerosol tubing 318.

In accordance with an embodiment, the ventilator 300 is a constant flow CPAP/ventilator circuit used for breathing support, which consists of an inspiratory line 302, an expiratory line 360, a patient interface 340, and a source of positive end expiratory pressure (PEEP valve or column of water). As an example, the ventilator 300 delivers an inspiratory stream of gas 304 via a feed line or inspiratory limb 302 to a splitter 312. The splitter 312 splits the flow of the inspiratory stream of ventilation gas 302 into two lines 314 and 315, which includes a carrier gas 316 and a ventilation gas 317, respectively. In accordance with an exemplary embodiment, the splitter 312 is a "Y" (Wye) or a "T" fitting, which splits the ventilator's inspiratory limb 302 into the two lines 314 and 315. In another exemplary embodiment, both a flow of approximately 3 liters per minute (LPM) of ventilation gas 317 and a flow of approximately 3 liters per minute (LPM) of carrier gas 316 can be separately generated by two ventilators. The carrier gas 316 is delivered via a carrier gas line 314 to the transition adapter 100, and ventilation gas 317 is delivered via a ventilation gas line 315 to the aerosol delivery connector 330. The carrier gas 316 passes through the transition adapter 100 while cooling and entraining the aerosol 234 in a laminar flow pattern. The entrained aerosol 240 is effectively carried to the aerosol delivery connector 330 reducing the amount of aerosol, which could potentially be lost due to impaction since the turbulence is minimized. The carrier gas 316 reduces the amount of aerosol 234, which could potentially be lost due to condensation since the relative temperature of the aerosol generated in this embodiment is approximately from 40° C. to 80° C., preferably from 40° C. to 60° C., at the point where the aerosol 234 exiting the heated capillary 232 meets the carrier gas 316 (approximately heated to 40° C.+/−5° C.) in the transition adapter 100. The entrained aerosol tube 318 at the exit of the transition adapter 100 has an initial temperature of 20° C. to 25° C. It should be understood that the temperature of the aerosol 234 can be higher than 60° C. and that the temperature of the carrier gas 316 can be adjusted upwards to maintain the optimal concentration of aerosol 234.

In an exemplary embodiment, the ventilation gas 317 is humidified to approximately 38° C. prior to entering the aerosol delivery connector 330. The temperatures of entrained aerosol 240 entering the aerosol delivery connector 330 and exiting the aerosol delivery connector 330 are maintained within the range of approximately 35° C. to 40°

C. In an exemplary embodiment, the ventilator's inspiratory flow 304 is humidified. In an exemplary embodiment, a non-humidified ventilation gas can be used.

For example, for a neonatal application, a flow rate of inspiratory gas of a total of approximately 6 liters per minute (LPM) is split is approximately 3 liters per minute (LPM) for the carrier gas 316 and approximately 3 liters per minute (LPM) for the ventilation gas 317. As shown, one limb of the Y or T fitting 312 is connected via the carrier gas tube 314 to the transition adapter 100. The other limb or ventilation gas 317 from the Y fitting 312 is humidified and travels through the ventilation gas tube 315 to a ventilation port 332 of the aerosol delivery connector 330. For the adult application, the Y fitting 312 would split the flow rate of approximately 10 to 120 liters per minute (LPM) into two limbs of approximately 5 to 100 LPM and approximately 115 to 20 LPM.

In accordance with an exemplary embodiment, the carrier gas line 314 is connected to the transition adapter 100 and has a diameter of approximately 3 millimeters to 12 millimeters. The ventilation gas tube 315, for example, has a diameter of approximately 10 or 12 millimeters, corrugated tubing with an approximately 15 millimeter conical end connector.

The entrained aerosol 240 is directed from the exit port 170 of the transition adapter 100 into an aerosol tubing 318, which provides an unobstructed flow through a fluid trap 320, and which maintains a laminar pattern of flow and reduces impaction of the entrained aerosol 240. For example, the entrained aerosol tubing 318 connecting the fluid trap 320 to the aerosol delivery connector 330 can be approximately 10 mm to 15 mm in diameter and preferably corrugated. In accordance with an exemplary embodiment, the length of the entrained aerosol tubing 318 is approximately 40 cm to approximately 100 cm. For example, the fluid trap 320 may have a capacity of at least 60 milliliters with an airway through the fluid trap 320 of approximately 15 to 22 millimeters in diameter.

As shown in FIG. 7A, the fluid trap 320 is located between the transition adapter 100 and the aerosol delivery connector 330, and is configured to trap condensed liquid or liquid from the entrained aerosol 240. In accordance with an exemplary embodiment, the entrained aerosol 240 entering the aerosol delivery connector 330 and the patient interface 340 from the entrained aerosol tube 318 has a temperature of approximately 35° C. to 39° C. The fluid trap 320 airway is minimally obstructed and the entrained aerosol tube 318 connected to the exit of the fluid trap 320 provides an unobstructed pathway to the aerosol delivery connector 330 maintaining laminar flow and reducing impaction.

For example, in accordance with an exemplary embodiment, the length of the entrained aerosol tube 318 is selected to cool the warm aerosol 234 to a desired or preferred patient interface aerosol temperature. In addition, the humidified air flowing within the ventilation gas line 315, which enters the aerosol delivery connector 330, is also preferably controlled to approximately 35° C. to 40° C. by a humidifier device 350. In accordance with an exemplary embodiment, the humidifier device 350 can be placed between the connector 312 (e.g., Wye fitting) and the aerosol delivery connector 330.

In accordance with an exemplary embodiment, the transition adapter 100 provides a smooth transition of aerosol 240 carried by the carrier gas 316 into the entrained aerosol tubing 318 through the fluid trap 320, which minimizes impaction of the generated aerosol 234 on the walls of the transition adapter 100 and relevant tubing. In addition, fewer large particles within the aerosol stream 234 impact the inner surface and tubing walls of the transition adapter 100, which can result in an average particle size of the entrained aerosol 240 of approximately 1.5 μm to 3.5 μm in diameter for the aerosolized drug.

In accordance with an exemplary embodiment, the split of the inspiratory flow 304 may be varied from approximately 3 liters per minute (LPM) for the carrier gas 316 and approximately 3 liters per minute (LPM) for ventilated gas 317 for a source flow rate of approximately 6 liters per minute (LPM) (e.g., a 3/3 split) to a 4/2 split with approximately 4 liters per minute (LPM) flow passing through the carrier gas tube 314 to the transition adapter 100 and approximately 2 liters per minute passing through the ventilation gas tube 315 and the humidifier 350. In addition, depending on the aerosol concentration and particle/droplet density, this split ratio may be changed to the 4/2 or a 5/1 ratio. For example, a range of ⅔ to a 5/1 ratio can be used, wherein between approximately 3 to 5 liters per minute (LPM) of inspiratory gas (or "oxygen/air") passes through the carrier gas tube 314 to the transition adapter 100. For higher levels of carrier gas passing through the transition adapter 100, the number of gas exit ports 156 within the transition adapter 100 can be increased and/or the diameter of the gas entry ports 154 and/or the gas exit ports 156 can be increased to accommodate a larger flow rate. For example, when the inspiratory flow 304 from the ventilator 300 is increased for therapeutic adult applications, larger carrier gas 316 flow rates can provide a more laminar flow of the entrained aerosol 240.

The aerosol delivery connector 330 is configured to deliver the entrained aerosol 240, with the ventilation gas 317 providing positive end expiratory pressure (PEEP), as an aerosolized active agent to a patient interface 340 with concomitant positive pressure ventilation. For example, the connector 330 can be as disclosed in U.S. Patent Publication No. 2011/0011395, which is incorporated herein in its entirety. As shown in FIG. 7A, the ventilation gas 317 travels through the ventilation gas tube 315 through the humidifier 350 to a ventilation port 332 of the aerosol delivery connector 330. In addition, the entrained aerosol 240 travels through the entrained aerosol tube 318 to the aerosol port 334 of the aerosol delivery connector 330. The flows 317 and 240 may be mixed with one another when the patient inspiratory flow exceeds the flow of the entrained aerosol 240 and delivered to the patient via the patient port 336 through the patient interface 340. If the patient inspiratory flow is equal or less than the flow of the entrained aerosol 240, the ventilation flow 317 is not mixed with the entrained aerosol 240 and flows through the aerosol delivery connector 330 for the purpose of providing positive end expiratory pressure (PEEP).

In accordance with an exemplary embodiment, the aerosol delivery connector 330 also includes an expiratory port 338, which is connected with an expiratory tube 360, which delivers an expiratory flow 362 back to the ventilator 300 after the expiratory flow 362 passes through a filter (not shown). For example, for an inspiratory flow 304 of approximately 6 liters per minute (LPM), the expiratory flow 362 can be approximately 6 liters per minute (LPM).

In another embodiment, as shown in FIGS. 7B and 7C, in a bubble CPAP, the expiratory flow 362 is not returned to the ventilator 300 but is directed to a source of back pressure, such as a water bath or reservoir 370.

Figure 8:
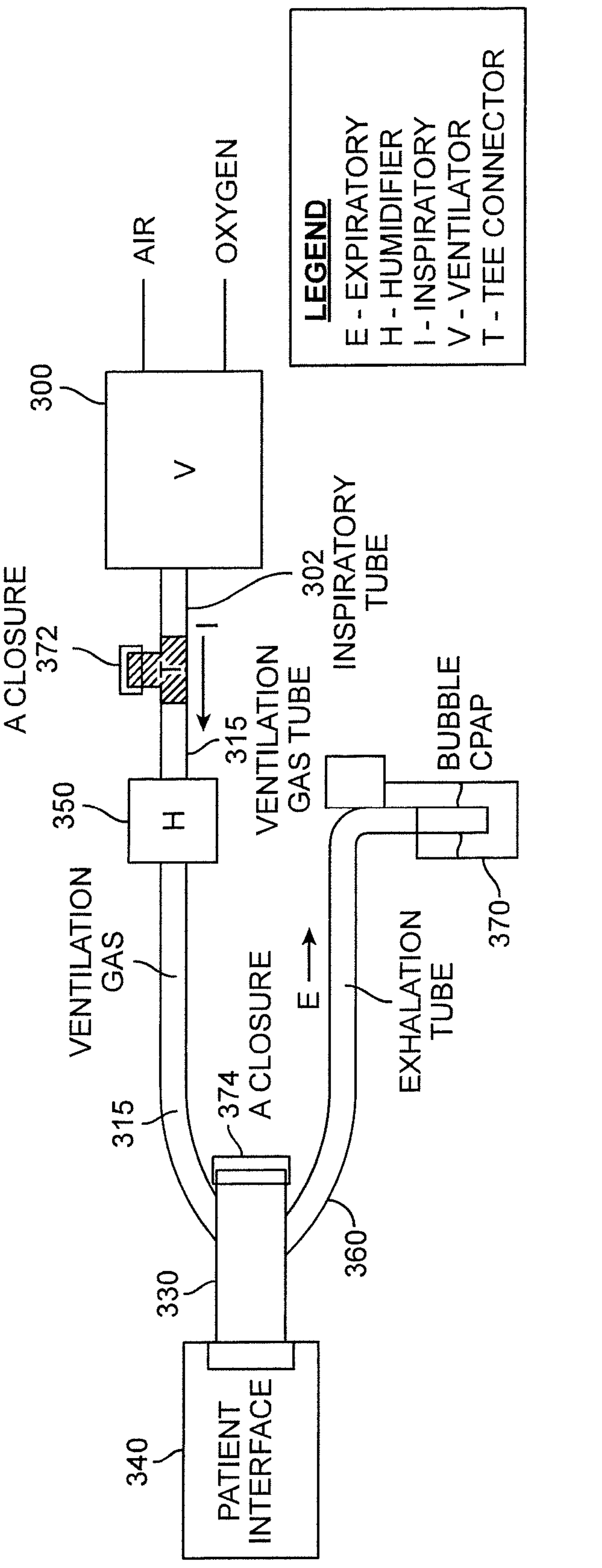
FIG. 8 is a schematic of a ventilator aerosol delivery system after the aerosol delivery has been completed and the patient is receiving only a ventilation gas.

When the therapy with the aerosolized drug is completed, the aerosol generator 230 can be paused or turned off, and the ventilation gas therapy can continue through the aerosol delivery connector 330 using either of the two lines or both, the entrained aerosol line 318 (filled with the carrier gas only) and/or the ventilation gas line 315. In accordance with an exemplary embodiment, as shown in FIG. 8, the splitter is capped with a closure 372 and the aerosol delivery connector is capped with a closure 374, which removes the entrained aerosol tube and the carrier gas tube from the circuit, and the ventilation gas line 315 is used to deliver the full volume of inspiratory gas to a patient. While in FIG. 8, the bubble CPAP is shown, it is understood that a close circuit CPAP where the exhaled gas is returned to the ventilator or any other ventilation circuit can be used. In another exemplary example with two ventilators 300 (e.g., as shown in FIG. 7C), the flow of aerosol in the tube can be paused by simply removing the aerosol tube from the aerosol delivery connector 330 and capping the aerosol delivery connector.

The patient interface 340 is selected to accommodate the type of ventilatory support to be administered. For example, invasive applications such as controlled, assisted or intermittent mandatory ventilation will utilize an endotracheal or tracheostomy tube as the patient interface 340. Non-invasive applications such as CPAP or BI-PAP may utilize nasal prongs or nasopharyngeal tubes, or a mask that covers the nose or both the nose and mouth as the patient interface 340. In accordance with an embodiment, the patient interface 340 is connected directly to the connector 330. In other embodiments, a length of tubing or a conduit 344 may be introduced between a patient port 336 of the connector 330 and the patient interface 340.

Figure 9A:
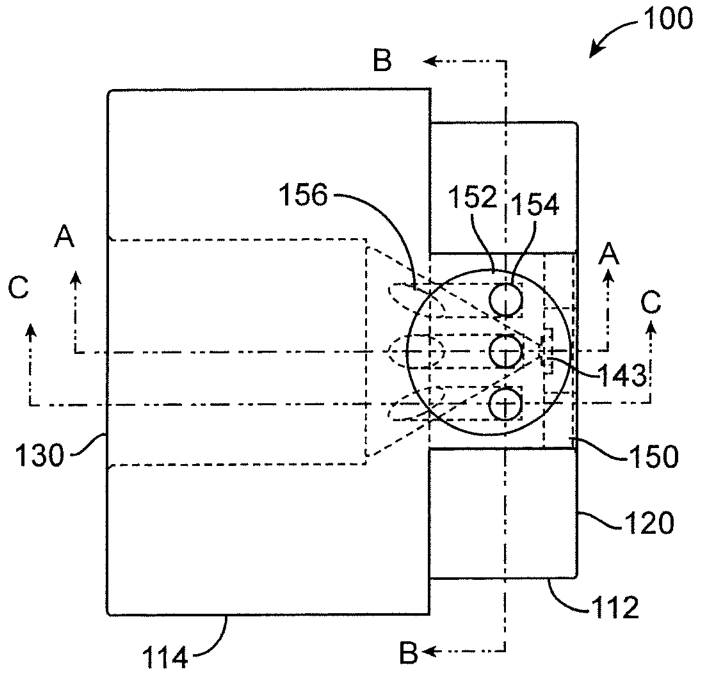
FIG. 9A is a side view of a transition adapter in accordance with an exemplary embodiment.

FIG. 9A is a side view of the transition adapter 100 as shown in FIG. 1 showing the gas connection port 150 in accordance with an exemplary embodiment in which the exit ports 156 are positioned on a distal end of the corresponding passages 158. As shown in FIG. 9A, the carrier gas connection port 150 is configured to receive a carrier gas line 314 from a ventilator 300. The carrier gas connection port 150 has a cylindrical cross-section 152 and a plurality of gas entry ports 154, each of which is in communication with a corresponding exit port 156. Each of the exit ports 156 delivers a stream of carrier gas to the inner cavity 170 of the transition adapter 100. For example, as shown in FIG. 9A, the plurality of gas entry ports 154 can be three (3) in number and can be positioned relative to one another in a vertical or straight line.

Figure 9B:
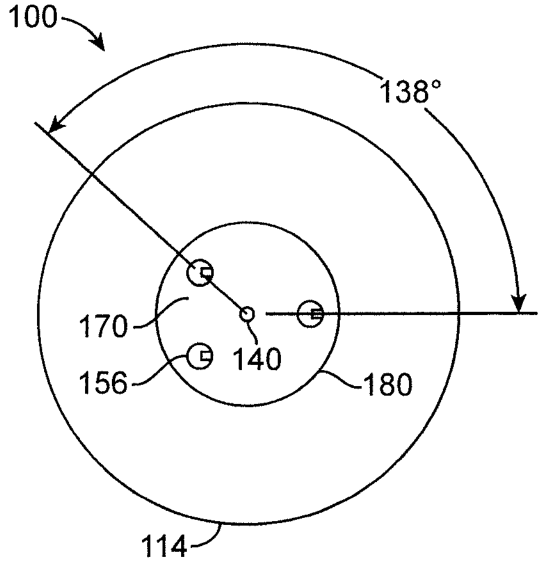
FIG. 9B is an end view of the transition adapter as shown in FIG. 9A in accordance with an exemplary embodiment.

FIG. 9B is an end view of the transition adapter 100 as shown in FIG. 9A in accordance with an exemplary embodiment. As shown in FIG. 9B, the distal end 130 of the transition adapter 100 can have a uniform inner diameter 176. In accordance with an exemplary embodiment, the plurality of exit ports 156 can be positioned within the proximal portion 172 of the inner cavity 170 along the conical portion 180. The plurality of gas entry ports 154 for receiving the stream of carrier gas 316 from the ventilator 300 can include at least three entry ports 154, each of the at least three entry ports 154 directing a stream of gas 316 to a corresponding gas exit port 156 located within the conical portion 180 of the inner cavity 170. The gas exit ports 156 are positioned on the distal end of the passages 158, which extend from the gas entry ports 154 located within the carrier gas connection port 140. In accordance with an exemplary embodiment, if the placement of the gas exit ports 156 on the distal end of the passages 158 is without an offset, the three gas exit ports 156 can vary from approximately 100 degrees to 140 degrees to one another around the aerosol passage 140 to accommodate manufacturing thereof. For example, as shown in FIG. 9B, two of the three exit ports 156 are approximately 138 degrees to one another.

Figure 9C:
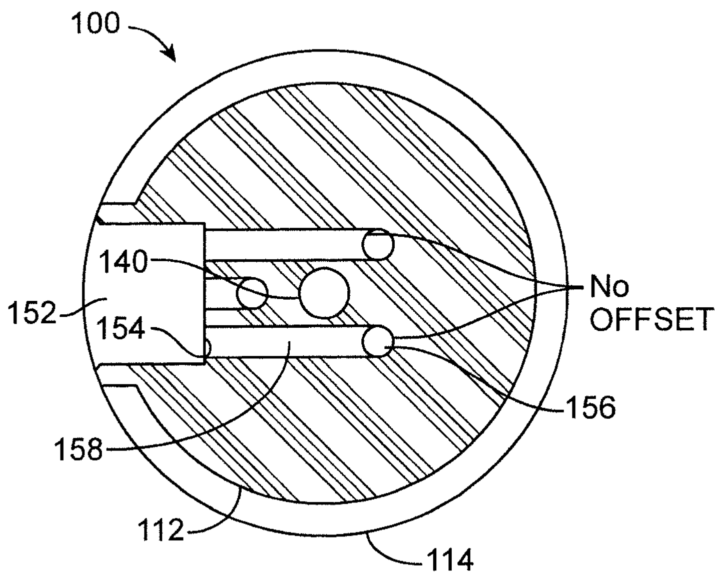
FIG. 9C is a cross-sectional view of the transition adapter as shown in FIG. 9A long the line B-B.

FIG. 9C is a cross-sectional view of the transition adapter 100 as shown in FIG. 9A along the line B-B. As shown in FIG. 9C, the plurality of gas entry ports 154 are each in communication with a corresponding exit port 156 via a plurality of passages 158. The passages 158 extend from a gas entry port 154 to a corresponding gas exit port 156. In accordance with an exemplary embodiment, the passages 158 are cylindrical. In accordance with this embodiment, each of the three exit ports 156 are located or positioned on a distal end of the corresponding passage 158.

Figure 9D:
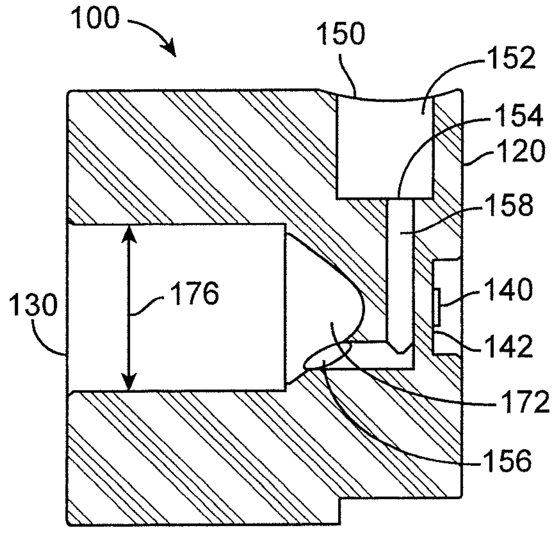
FIG. 9D is a cross-sectional view of the transition adapter as shown in FIG. 9A along the line C-C.

FIG. 9D is a cross-sectional view of the transition adapter 100 as shown in FIG. 9D along the line C-C. As shown in FIG. 9D, each of the passages 158 can extend inward from the carrier gas connection port 150 towards the aerosol passage 140 and then transitions toward the inner cavity 170. Each of the passages 158 has a proximal portion extending from the entry port 154 to a transition, and a distal portion, which extends from the transition to the exit port 156. The transition of the passage 158 from the proximal portion to the distal portion can be at a right angle to one another, or alternatively, the transition can be rounded or have a curvature thereto.

As shown in FIG. 9D, the inner cavity 170 has a proximal portion 172 having a conical section, which expands outward from the aerosol passage 140 towards the distal end 130 of the housing 110. In accordance with an exemplary embodiment, the distal portion 174 of the inner cavity 170 can have a slightly tapered inner diameter. In accordance with an exemplary embodiment, the plurality of corresponding gas exit ports 156 are positioned within the proximal portion 172 of the inner cavity 170.

Figure 9E:
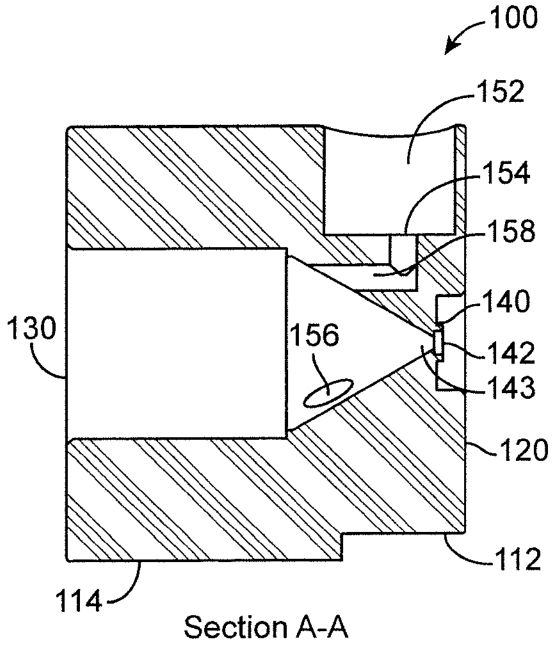
FIG. 9E is a cross-sectional view of the transition adapter as shown in FIG. 9A along the line A-A.

FIG. 9E is a cross-sectional view of the transition adapter as shown in FIG. 9A along the line A-A. As shown in FIG. 9E, the passages 158 can extend inward from the carrier gas connection port 150 towards the aerosol passage 140 and then transitions toward the inner cavity 170.

Figure 10A:
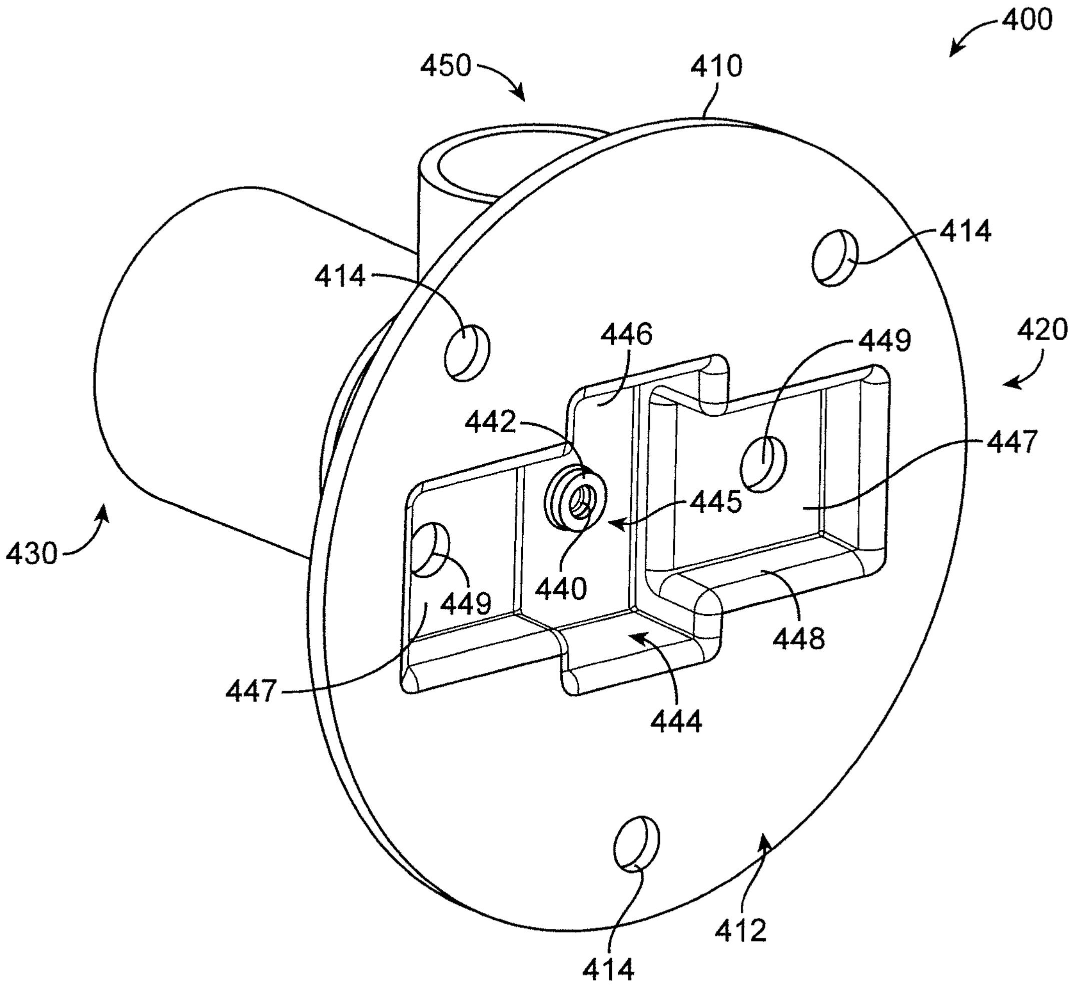
FIG. 10A is a perspective view of a transition adapter in accordance with an exemplary embodiment.

FIG. 10A is a perspective view of a transition adapter 400 in accordance with another exemplary embodiment. As shown in FIG. 10A, the transition adapter 400 includes a housing 410 having a proximal end 420 and a distal end 430. The proximal end 420 has an aerosol passage 440 for receiving an aerosol 234 produced by a heated capillary 232 (FIGS. 7A-7B) of an aerosol generator 230 (FIGS. 7A-7B). The aerosol passage 440 preferably includes a coupling port 442, which contains a connection to a distal end (FIGS. 7A-7B) of the heated capillary 232. The aerosol 234 enters into an inner cavity 470 (FIGS. 10B and 10C) within the transition adapter 400 through the aerosol passage 440 where the aerosol 234 is at least partially encircled and carried forward by parallel streams of carrier gas 316, which are originated from a source of gas or ventilator 300 and introduced into the transition adapter through the plurality of gas entry ports 454 (FIG. 10C) to form an entrained aerosol 240 (FIGS. 7A-7B) which is a combination of the aerosol 234 and the carrier gas 316. In accordance with an exemplary embodiment, the source of gas 300 (see FIGS. 7A-7B) is a continuous positive airway pressure (CPAP) ventilator, which produces inspiratory flow 302 and receives filtered expiratory flow 362 (FIGS. 7A-7B).

As shown in FIG. 10A, the aerosol passage 440 has a coupling port 442, which receives the distal end of the heated capillary 232 of the aerosol generator 230, which is positioned within a cavity 444 on the proximal end 420 of the housing 410. In accordance with an exemplary embodiment, the cavity 444 can include an aerosol coupling end wall 446 and a pair of end side walls 447. In accordance with an exemplary embodiment, the aerosol coupling end wall 446 is recessed in comparison to the pair of end side walls 447, which allows a compression ring or O-ring seal (not shown) to be positioned within a recessed portion of the cavity 444. The compression ring or O-ring seal directs the aerosols 234 generated by the aerosol generated 230 into aerosol passage 440. In accordance with an exemplary embodiment, the aerosol end wall 446 is generally rectangular having a height greater than its width. The height of the aerosol end wall 446 is slightly greater than a height of each of the side end walls 447, which produces a second cavity 445 within cavity 444. The second cavity 445 has a generally rectangular shape with a depth sufficient to receive the compression ring or O-ring seal.

In accordance with an exemplary embodiment, each of the side end walls 447 can include one or more openings or bores 449, which secures the distal end of the aerosol generator 230 to the transition adapter 400. The cavity 444 also includes a plurality of side walls 448, which extend outward from an outer edge of the aerosol coupling end wall 446 and the side end walls 448 to form a generally elongated rectangular cavity 444. In accordance with an exemplary embodiment, the cavity 444 is configured to provide a secure method of coupling the distal end of the aerosol generator 230 to the coupling port 442 of the aerosol passage 440. The aerosol passage 440 is in communication with the inner cavity 470 (FIGS. 10B and 10C) of the transition adapter 400.

In accordance with an exemplary embodiment, the proximal end 420 of the housing 410 includes a flange 412. The flange 412 can include one or more openings or bores 414, which can be configured to be attachable to a distal portion of the aerosol generator 230. The housing 410 also includes a carrier gas connection port 450, which can extend perpendicular to a face of the flange 412 and is configured to receive a carrier gas line 314 (FIGS. 7A-7B). The gas line 314 transports a stream of carrier gas 316 (FIGS. 7A-7B) from the ventilator 300 to the transition adapter 400.

Figure 10B:
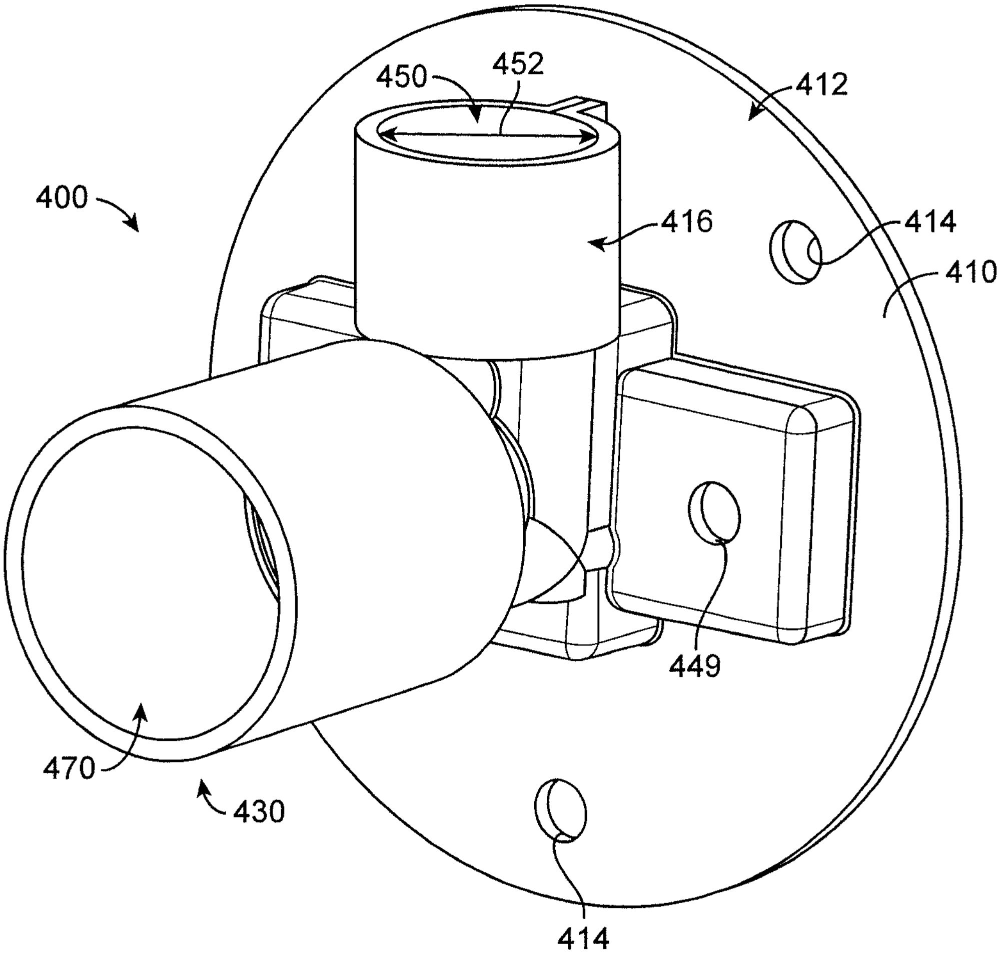
FIG. 10B is another perspective view of the transition adapter as shown in FIG. 10A in accordance with an exemplary embodiment.
Figure 10C:
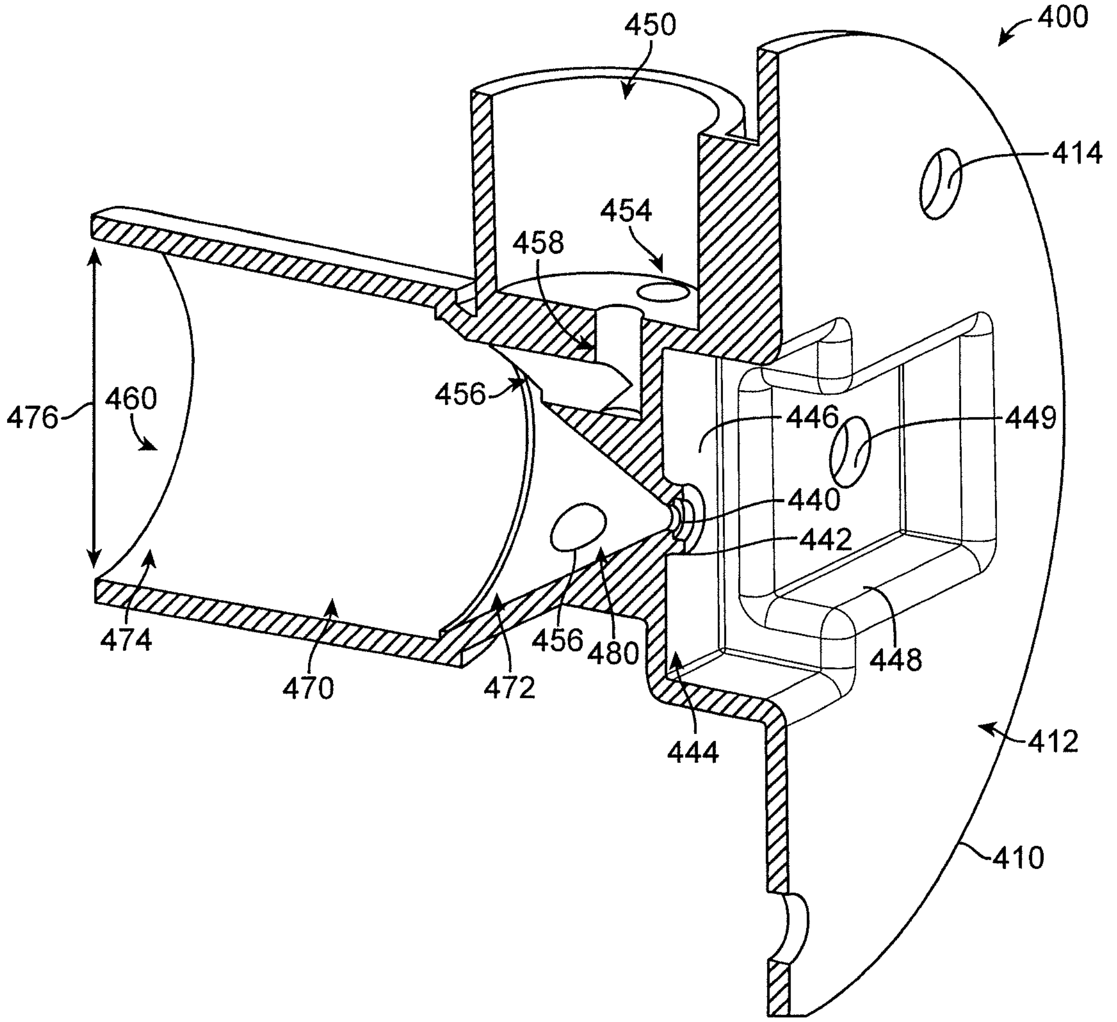
FIG. 10C is a partial cut-out view of the transition adapter as shown in FIGS. 10A and 10B in accordance with an exemplary embodiment.

FIG. 10B is another perspective view of the transition adapter as shown in FIG. 10A in accordance with an exemplary embodiment. As shown in FIG. 10B, the housing 410 of the transition adapter 400 includes a cylindrical body 416, which includes a carrier gas connection port 450 for receiving the carrier gas 316 via a carrier gas line 314 from a ventilator 300 (FIGS. 7A-7B). The carrier gas connection port 450 has a cylindrical cross-section 452, which is in communication with a plurality of gas entry ports 454 and a plurality of corresponding gas exit ports 456 via passages 458 (FIG. 10C). Each of the gas exit ports 456 delivers a stream of carrier gas 316 to the inner cavity 470 of the transition adapter 400.

FIG. 10C is a partial cut-out view of the transition adapter as shown in FIGS. 10A and 10B in accordance with an exemplary embodiment. As shown in FIG. 10C, the aerosol passage 440 is in communication with the inner cavity 470 which receives the aerosol 234 from the heated capillary 232 and the streams of carrier gas 316 from the plurality of gas exit ports 456 and directs the streams of carrier gas 316 to flow in parallel with the main direction of the flow of aerosol 234. The streams of carrier gas 316 at least partially encircle the aerosol flow path within the inner cavity and carry the aerosol 234 toward the distal end 430 such that the entrained aerosol 240 is created within an inner cavity 470. The entrained aerosol 240 exits the transition adapter 400 through an exit port 460 at the distal end 430 and flows into an aerosol tube 318 (FIGS. 7A-7B).

As shown in FIG. 10C, the inner cavity 470 has a proximal portion 472 having a conical section 480, which expands outward from the aerosol passage 440 towards the distal end 430 of the housing 410. In accordance with an exemplary embodiment, the walls of the conical section 480 of the proximal portion 472 of the inner cavity 470 form an angle of approximately 45 degrees to approximately 75 degrees (for example, an approximately 60 degree cone). The distal portion 474 of the inner cavity 470 can also have a slightly tapered inner diameter. In accordance with an exemplary embodiment, the plurality of corresponding gas exit ports 456 are positioned within the proximal portion 472 of the inner cavity 470 along the conical section 480.

In accordance with an exemplary embodiment, the plurality of gas entry ports 454 for receiving the carrier gas 316 from the ventilator 300 has at least two entry ports 454, and preferably at least three entry ports 454 or more, and thereby splitting the carrier gas in a plurality of carrier gas streams. From each of the entry ports 454, a stream of carrier gas 316 is further directed to a corresponding number of gas exit ports 456, which are located within the conical section 480 of the inner cavity 470. In accordance with an exemplary embodiment, the gas exit ports 456 deliver a plurality of streams of carrier gas 316 such that the streams of carrier gas 316 at least partially encircle and flow in parallel to the main flow of aerosol 234 delivered from the aerosol passage 440. Since the aerosol 234 may have a plume with sprays angling from the main direction toward the exit from the transition adapter 400, the term “main flow of aerosol” is used to indicate the direction along which carrier gas 316 will be flowing. In accordance with an exemplary embodiment, the plurality of gas exit ports 456 are placed at a distance from the aerosol passage 440 in a pattern that allows the plurality of carrier gas streams 316 to at least partially encircle the flow of the aerosol 234 after the aerosol has entered the conical section 480 and has passed the gas exit ports 456.

In accordance with an exemplary embodiment, each of the plurality of exit ports 456 are approximately 1 to 10 millimeters in diameter and located at an approximately 3 to 20 millimeter radius from a central axially extending aerosol passage 443 from which the aerosol 234 enters the housing 410 of the transition adapter 400. The exit port 460 at the distal end 474 of the transition adapter 400 forms a flow channel having an inner diameter 476, for example, of approximately 22 mm to 50 mm.

Figure 11A:
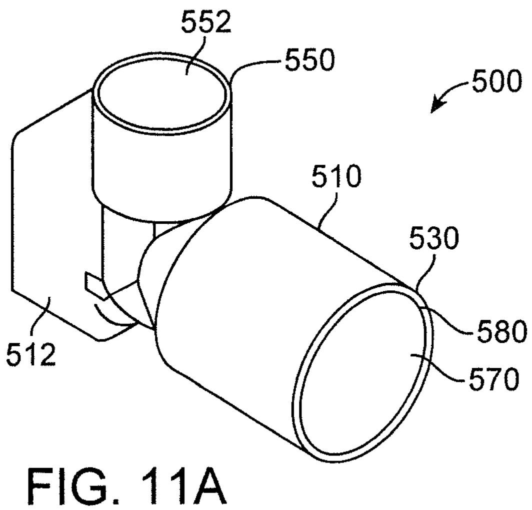
FIG. 11A is a perspective view of a transition adapter in accordance with a further exemplary embodiment.
Figure 11B:
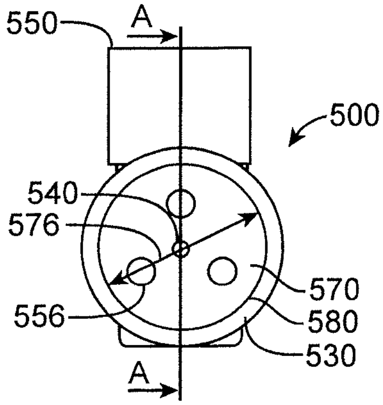
FIG. 11B is an end view of the transition adapter as shown in FIG. 11A in accordance with an exemplary embodiment.
Figure 11C:
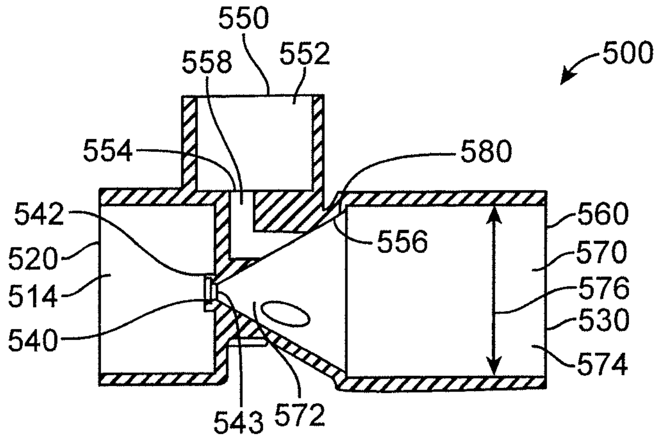
FIG. 11C is a cross-sectional view of the transition adapter as shown in FIG. 11A in accordance with an exemplary embodiment.
Figure 11D:
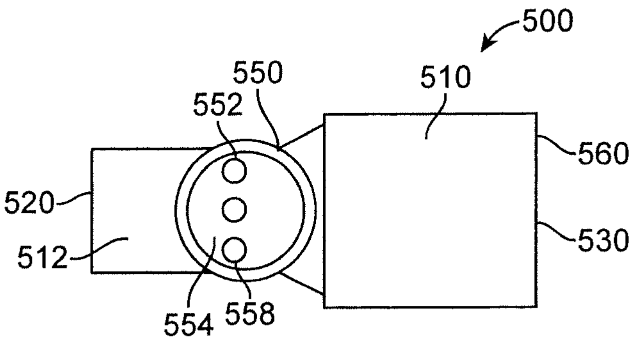
FIG. 11D is a side view of the transition adapter as shown in FIG. 11A in accordance with an exemplary embodiment.

FIG. 11A is a perspective view of a transition adapter 500 in accordance with another exemplary embodiment. As shown in FIG. 11A, the transition adapter 500 includes a housing 510 having a proximal end 520 and a distal end 530 (FIGS. 11B-11D). The proximal end 520 has an aerosol passage 540 for receiving an aerosol 234 produced by a heated capillary 232 (FIGS. 7A-7B) of an aerosol generator 230 (FIGS. 7A-7B). The aerosol passage 540 preferably includes a coupling port 542, which contains a connection to a distal end (FIGS. 7A-7B) of the heated capillary 232. The aerosol 234 enters into an inner cavity 570 within the transition adapter 500 through the aerosol passage 540 where the aerosol 234 is at least partially encircled and carried forward by parallel streams of carrier gas 316, which are originated from a source of gas or ventilator 300 and introduced into the transition adapter through the plurality of gas entry ports 554 (FIG. 11C) to form an entrained aerosol 240 (FIGS. 7A-7B) which is a combination of the aerosol 234 and the carrier gas 316.

FIG. 11B is an end view of the transition adapter as shown in FIG. 11A in accordance with an exemplary embodiment. As shown in FIG. 11B, the housing 510 of the transition adapter 500 includes a carrier gas connection port 550 for receiving the carrier gas 316 via a carrier gas line 314 from a ventilator 300 (FIGS. 7A-7B). The carrier gas connection port 550 has a cylindrical cross-section 552, which is in communication with a plurality of gas entry ports 554 and a plurality of corresponding gas exit ports 556 via at least one passage 558 (FIG. 11C). Each of the gas exit ports 556 delivers a stream of carrier gas 316 to the inner cavity 570 of the transition adapter 500.

FIG. 11C is a cross-sectional view of the transition adapter as shown in FIGS. 11A and 11B in accordance with an exemplary embodiment. As shown in FIG. 11C, the aerosol passage 540 has a coupling port 542, which receives the distal end of the heated capillary 232 of the aerosol generator 230, and which is positioned within a flange or aerosol housing 512 on the proximal end 520 of the transition adapter 500. The flange or aerosol housing 512 has an inner portion or cavity 514, which is configured to receive the aerosol generator 230. In accordance with an exemplary embodiment, the inner portion or cavity 514 of the flange or aerosol housing 512, for example, can have any suitable geometrical shape, preferably the shape with a rectangular, a cylindrical, or a triangular cross-section. In accordance with an exemplary embodiment, the inner portion 514 of the flange or aerosol housing 512 is configured to allow a compression ring or O-ring seal (not shown) to be positioned within a recessed portion of the flange or housing 512. The compression ring or O-ring seal directs the aerosols 234 generated by the aerosol generator 230 into the aerosol passage 540. The inner portion or cavity 514 is configured to provide a secure method of coupling the distal end of the aerosol generator 230 to the coupling port 542 of the aerosol passage 540. The aerosol passage 540 is in communication with the inner cavity 570 (FIG. 11C) of the transition adapter 500.

As shown in FIG. 11C, the aerosol passage 540 is in communication with the inner cavity 570 which receives the aerosol 234 from the heated capillary 232 and the streams of carrier gas 316 from the plurality of gas exit ports 556 and directs the streams of carrier gas 316 to flow in parallel with the main direction of the flow of aerosol 234. The carrier gas streams 316 at least partially encircle the aerosol flow path within the inner cavity and carry the aerosol 234 toward the distal end 530 such that the entrained aerosol 240 is created within the inner cavity 570. The entrained aerosol 240 exits the transition adapter 500 through an exit port 560 at the distal end 530 and flows into an aerosol tube 318 (FIGS. 7A-7B).

The inner cavity 570 has a proximal portion 572 having a conical section 580, which expands outward from the aerosol passage 540 towards the distal end 530 of the housing 510. In accordance with an exemplary embodiment, the walls of the conical section 580 of the proximal portion 572 of the inner cavity 570 form an angle of approximately 45 degrees to approximately 75 degrees (for example, an approximately 60 degree cone). The distal portion 574 of the inner cavity 570 can also have a slightly tapered inner diameter. In accordance with an exemplary embodiment, the plurality of corresponding gas exit ports 556 are positioned within the proximal portion 572 of the inner cavity 570 along the conical section 580.

In accordance with an exemplary embodiment, the gas exit ports 556 deliver a plurality of streams of carrier gas 316 such that they at least partially encircle and flow in parallel to the main flow of aerosol 234 delivered from the aerosol passage 540. Since the aerosol may have a plume with sprays angling from the main direction toward the exit from the transition adapter, the term "main flow of aerosol" is used to indicate the direction along which carrier gas 316 will be flowing. In accordance with an exemplary embodiment, the plurality of gas exit ports 556 are placed at a distance from the aerosol passage 540 in a pattern that allows the plurality of carrier gas streams to at least partially encircle the flow of the aerosol 234 after the aerosol has entered the conical section 580 and has passed the gas exit ports 556.

As shown in FIG. 11D, the plurality of gas entry ports 554 for receiving the carrier gas 316 from the ventilator 300 has at least two entry ports 554, and preferably at least three entry ports 554 or more and thereby splitting the carrier gas 316 into a plurality of carrier gas streams. From the entry ports 554, a stream of carrier gas is further directed to a corresponding number of gas exit ports 556, which are located within the conical section 580 of the inner cavity 570.

In accordance with an exemplary embodiment, each of the plurality of exit ports 556 are approximately 1 to 10 millimeters in diameter and located at an approximately 3 to 20 millimeter radius from a central axially extending aerosol passage 543 from which the aerosol 234 enters the housing 510 of the transition adapter 500. The exit port 560 at the distal end 574 of the transition adapter 500 forms a flow channel having an inner diameter 576, for example, of approximately 22 mm to 50 mm.

Figure 12A:
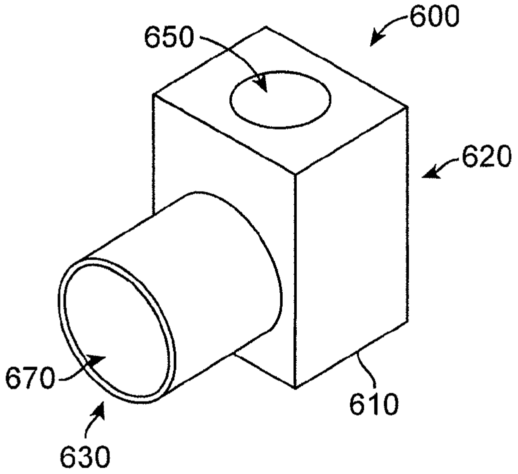
FIG. 12A is a perspective view of a transition adapter in accordance with an exemplary embodiment.

FIG. 12A is a perspective view of a transition adapter 600 in accordance with another exemplary embodiment. As shown in FIG. 12A, the transition adapter 600 includes a housing 610 having a proximal end 620 and a distal end 630. The proximal end 620 has an aerosol passage 640 (FIG. 12D) for receiving an aerosol 234 produced by a heated capillary 232 (FIGS. 7A-7B) of an aerosol generator 230 (FIGS. 7A-7B). The aerosol passage 640 preferably includes a coupling port 642, which contains a connection to a distal end (FIGS. 7A-7B) of the heated capillary 232. The aerosol 234 enters into an inner cavity 670 within the transition adapter 600 through the aerosol passage 640 where the aerosol 234 is at least partially encircled and carried forward by parallel streams of carrier gas 316, which are originated from a source of gas or ventilator 300 and introduced into the transition adapter through a plurality of gas exit ports 656 (FIG. 12B) to form an entrained aerosol 240 (FIGS. 7A-7B) which is a combination of the aerosol 234 and the carrier gas 316.

Figure 12B:
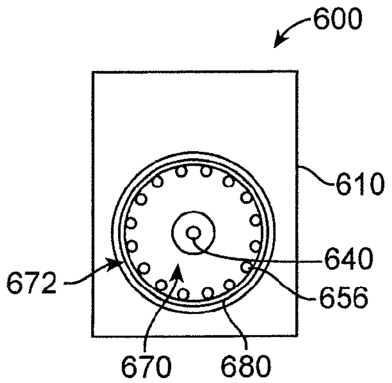
FIG. 12B is an end view of the transition adapter as shown in FIG. 12A in accordance with an exemplary embodiment.

FIG. 12B is an end view of the transition adapter 600 as shown in FIG. 12A in accordance with an exemplary embodiment. As shown in FIG. 12B, the distal end 630 of the transition adapter 600 has an inner cavity 670. The inner cavity 670 has a proximal portion 672 having a conical section 680, which expands outward from the aerosol passage 640 towards the distal end 630 of the housing 610. The source of gas or ventilator 300 is introduced into the inner cavity 670 through a plurality of gas exit ports 656, which surrounds the aerosol port 640 to form the entrained aerosol 240.

Figure 12C:
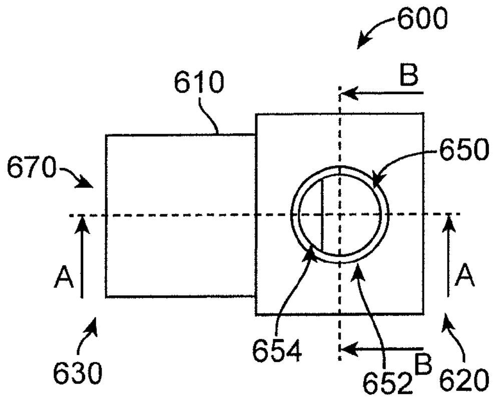
FIG. 12C is a side view of the transition adapter as shown in FIG. 12A in accordance with an exemplary embodiment.

FIG. 12C is a side view of the transition adapter 600 in accordance with an exemplary embodiment. As shown in FIG. 12C, the housing 610 of the transition adapter 600 includes a carrier gas connection port 650 for receiving the carrier gas 316 via a carrier gas line 314 from a ventilator 300 (FIGS. 7A-7B).

Figure 12D:
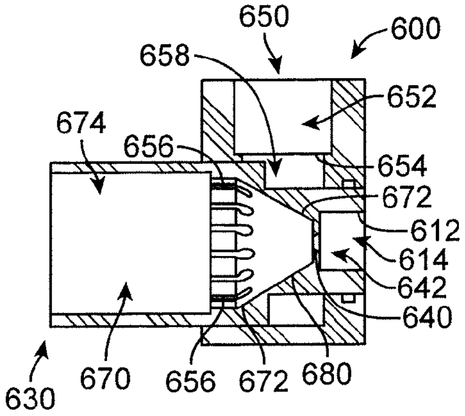
FIG. 12D is a cross-sectional view of the transition adapter as shown in FIG. 12C long the line A-A.

FIG. 12D is a cross-sectional view of the transition adapter as shown in FIG. 12C long the line A-A. As shown in FIG. 12D, the aerosol passage 640 has a coupling port 642, which receives the distal end of the heated capillary 232 of the aerosol generator 230, and is positioned within an aerosol housing 612 on the proximal end 620 of the transition adapter 600. The aerosol housing 612 has an inner portion or cavity 614, which is configured to receive the aerosol generator 230. In accordance with an exemplary embodiment, the inner portion or cavity 614 of the aerosol housing 612, for example, can have any suitable geometrical shape, preferably the shape with a rectangular, a cylindrical, or a triangular cross-section. In accordance with an exemplary embodiment, the inner portion 614 of the flange or aerosol housing 612 is configured to allow a compression ring or O-ring seal (not shown) to be positioned within a recessed portion of the flange or housing 612. The compression ring or O-ring seal directs the aerosols generated by the aerosol generated into aerosol passage 640. The inner portion or cavity 614 is configured to provide a secure method of coupling the distal end of the aerosol generator 230 to the coupling port 642 of the aerosol passage 640. The aerosol passage 640 is in communication with the inner cavity 670 of the transition adapter 600.

As shown in FIG. 12D, the carrier gas connection port 650 has a cylindrical cross-section 652, which is in communication with a source of gas 300, which can be introduced into the inner cavity 670 via a single gas entry port 654. The single gas entry port 654 is in communication with a single gas passage 658, which is in communication with a plurality of openings or exit ports 656 along the conical section 680 of the inner cavity 670. In accordance with an exemplary embodiment, the walls of the conical section 680 of the proximal portion 672 of the inner cavity 670 form an angle of approximately 45 degrees to approximately 75 degrees (for example, an approximately 60 degree cone). The distal portion 674 of the inner cavity 670 can also have a slightly tapered inner diameter. In accordance with an exemplary embodiment, the plurality of corresponding gas exit ports 656 are positioned within the proximal portion 672 of the inner cavity 670 along the conical section 680

Figure 12E:
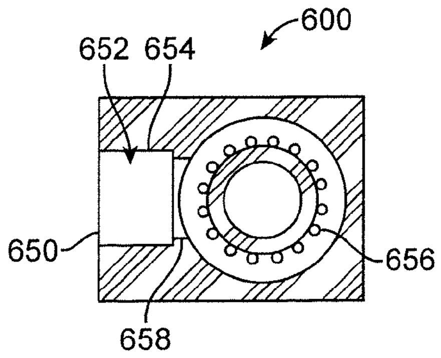
FIG. 12E is a cross-sectional view of the transition adapter as shown in FIG. 12C along the line B-B.

FIG. 12E is a cross-sectional view of the transition adapter 600 as shown in FIG. 12C along the line B-B. As shown in FIG. 12E, the carrier gas connection port 650 has a cylindrical cross-section 652, which is in communication with a source of gas 300, which can be introduced into the inner cavity 670 via a single gas entry port 654. The single gas entry port 654 is in communication with a single gas passage 658, which is in communication with a plurality of openings or exit ports 656 along the conical section 680.

In accordance with an exemplary embodiment, the length of each of the carrier gas passages 158, 458, 558, 658 within the transition adapter 100, 400, 500, 600 is selected to be approximately the same to ensure the uniformity of the speed and volume of the carrier gas.

While various embodiments have been disclosed, it is to be understood that variations and modifications may be resorted to as will be apparent to those skilled in the art. Particularly, the outer shape of the transition adapter can be modified without affecting the inner structure. Such variations and modifications are to be considered within the purview and scope of the claims appended hereto.

What is claimed is:

1. An aerosol transition adapter for delivering an aerosolized active agent to a patient receiving ventilation support, the aerosol transition adapter comprising:

a housing having a proximal end and a distal end, the proximal end having an aerosol passage for receiving an aerosol produced by a source of aerosol comprising an aerosolized active agent and the distal end having an exit port, the housing having a length between the distal end and the proximal end;

a carrier gas connection port configured to receive a carrier gas from a positive pressure gas source, which is in communication with a plurality of carrier gas exit ports, and wherein the plurality of carrier gas exit ports are arranged adjacent to the aerosol passage in a pattern that at least partially encircles a flow of aerosol from the aerosol passage;

a carrier gas conduit connected to the carrier gas connection port, wherein the carrier gas conduit is in communication with the positive pressure gas source; and an inner cavity, which is adapted to receive the aerosol from the aerosol passage and the carrier gas from the plurality of carrier gas exit ports and to direct streams of carrier gas to at least partially encircle and flow in parallel with a main direction of a flow of the aerosol along the length of the housing toward the exit port, the inner cavity having a proximal portion having a conical inner wall, which extends outward to an inner wall of a distal portion of the inner cavity, and wherein the plurality of carrier gas exit ports are located on the conical inner wall.

2. The adapter of claim 1, wherein the plurality of carrier gas exit ports are positioned on the conical inner wall at an equidistance from a center of the aerosol passage.

3. The adapter of claim 1, wherein the housing includes a cylindrical proximal portion and a cylindrical distal portion, and wherein the cylindrical proximal portion includes the carrier gas connection port configured to receive the carrier gas from the positive pressure gas source.

4. The adapter of claim 3, wherein an outer diameter of the cylindrical proximal portion is less than an outer diameter of the cylindrical distal portion.

5. The adapter of claim 1, wherein the carrier gas connection port for receiving the carrier gas from the gas source includes at least one gas entry port for receiving the carrier gas, the at least one gas entry port directing a stream of carrier gas to the plurality of gas exit ports.

6. The adapter of claim 5, wherein the at least one gas entry port comprises at least three gas entry ports, and the plurality of the carrier gas exit ports comprises at least three gas exit ports with a corresponding gas exit port for each of the gas entry ports.

7. The adapter of claim 6, wherein the at least three gas exit ports are equally spaced around the aerosol passage.

8. The adapter of claim 1, wherein each of the plurality of carrier gas exit ports is approximately 1 to 10 millimeters in diameter and located at approximately a 3 to 20 millimeter radius from a central axis of the aerosol passage.

9. The adapter of claim 1, wherein the exit port of the transition adapter has an inner diameter of approximately 22 mm to approximately 50 mm.

10. The adapter of claim 1, comprising:

a flange, which is attached to the proximal end of the housing.

11. The adapter of claim 10, comprising:

a cavity within the flange, which is configured to be attachable to the source of aerosol.

12. An aerosol delivery system, comprising:

an aerosol generator for producing an aerosol;

a positive pressure generator for producing a pressurized ventilation gas;

a splitter for splitting the pressurized ventilation gas into the carrier gas and a ventilation gas and a conduit from the positive pressure generator to the splitter;

an aerosol transition adapter according to claim 1 and arranged to combine the aerosol produced by the aerosol generator with the carrier gas from the splitter, and which forms an entrained aerosol;

an aerosol delivery connector having a port for receiving the entrained aerosol, a port for entry of the ventilation gas, a patient-aerosol interface port for delivering the entrained aerosol from the aerosol transition adapter and the ventilation gas from the splitter to a patient, and a port for exit of expiration gas from the patient; and a patient interface for receiving the entrained aerosol and the ventilation gas from the aerosol delivery connector.

13. The system of claim 12, further comprising a conduit for delivering the entrained aerosol and the ventilation gas from the patient-aerosol interface port to the patient interface.

14. The system of claim 12, further comprising a humidifier located between the splitter and the aerosol delivery connector for humidifying the ventilation gas before the ventilation gas enters the aerosol delivery connector.

15. The system of claim 14, wherein a ventilation flow tube connecting the splitter to the humidifier is a corrugated tubing having a diameter of approximately 10 to 12 millimeters in diameter with an approximately 15 millimeter conical end connector.

16. The system of claim 12, comprising:

a fluid trap, which is located between the aerosol transition adapter and the aerosol delivery connector, and wherein the fluid trap is configured to entrap condensed liquid or liquid from the entrained aerosol.

17. The system of claim 16, wherein the fluid trap has a capacity of at least 60 milliliters, and an airway through the fluid trap is 15 to 22 millimeters in diameter.

18. The system of claim 17, wherein an aerosol tube connecting the fluid trap to the aerosol delivery connector is a corrugated tubing having a diameter of approximately 10 to 15 millimeters and a length of approximately 40 to 100 centimeters.

19. The system of claim 12, wherein the splitter for splitting the pressurized ventilation gas from the ventilator into the carrier and ventilation gas flows is a Wye or Tee fitting.

20. The system of claim 12, further comprising a source of liquid formulation containing a lung surfactant adapted for delivery as the aerosol to an infant's lungs, and wherein the source of liquid formulation is configured to be delivered to the aerosol generator.

21. The system of claim 12, wherein the ventilator is configured to supply an inspiratory flow of gas at a flow rate of about 1 to 10 L/min (liters per minute).

22. The system of claim 12, wherein the aerosol generator is at least one of a heated capillary aerosol generator, a nebulizer, a soft mist generator, a metered dose inhaler, a liquid dose instillation device, and/or a dry powder inhaler.

23. The system of claim 12, wherein the aerosol generator comprises more than one aerosol generator.

24. The system of claim 12, wherein the port for exit of expiration gas from the patient is connected to an expiratory tube, which is configured to deliver the expiration gas to the positive pressure generator after passing through a filter.

25. The system of claim 12, wherein the port for exit of expiration gas from the patient is connected to a source of back pressure.

26. The system of claim 25, wherein the source of back pressure is a water bath or reservoir.

27. The system of claim 12, wherein the splitter and the aerosol delivery connector each have a closure, which allows the system to deliver the ventilation gas to the patient without the aerosol.

28. An aerosol delivery system, comprising:

an aerosol generator for producing an aerosol;

a plurality of positive pressure generators, wherein at least one of the plurality of positive pressure generators is a positive pressure generator for producing a ventilation gas and at least one of the plurality of positive pressure generators is a positive pressure generator for producing a carrier gas;

an aerosol transition adapter according to claim 1 and arranged to combine the aerosol produced by the aerosol generator with the carrier gas to form an entrained aerosol; and a patient interface for receiving the entrained aerosol and the ventilation gas.

29. A method of producing an entrained aerosol comprising:

generating an aerosol;

providing a source of carrier gas from a ventilator; and combining the aerosol and the carrier gas in the aerosol transition adapter according to claim 1 by dividing the carrier gas into a plurality of streams of carrier gas, which are at least partially encircling and flowing in parallel with the aerosol to form an entrained aerosol.

30. The method of claim 29, comprising:

splitting an inspiratory flow of gas from the ventilator into a carrier gas flow and a ventilation gas flow, wherein the carrier gas is combined with the aerosol in the aerosol transition adapter to form the entrained aerosol and the ventilation gas is delivered to an aerosol delivery connector, which receives the entrained aerosol and the ventilation gas for delivery to a patient.

31. The method of claim 29, further comprising delivering the entrained aerosol and the ventilation gas to the patient via a patient interface.

32. The method of claim 31, wherein, for a neonatal application, providing the inspiratory flow from the ventilator at a rate of approximately six liters per minute, and splitting the inspiratory flow rate from the ventilator into approximately three liters per minute into a carrier gas conduit and approximately three liters per minute into a ventilation gas conduit.

33. The method of claim 32, wherein the entrained aerosol enters the patient interface at approximately 35° C. to 39° C.

34. The method of claim 30, wherein the ventilation gas enters the aerosol delivery connector at approximately 35° C. to 39° C.

35. The method of claim 30, comprising:

directing an exhaled gas from a patient to the ventilator such that a volume of an inspiratory gas originating from the ventilator is approximately equal to a volume of the exhaled gas directed to the ventilator.

36. The method of claim 30, wherein the step of generating the aerosol includes generating the aerosol with a heated capillary.

37. The method of claim 30, wherein the step of generating the aerosol includes generating the aerosol with a nebulizer, a soft mist generator, a metered dose inhaler, a liquid dose instillation device, or a dry powder inhaler.

38. The method of claim 30, wherein the ventilation gas is a humidified ventilation gas.

* * * * *